(12) United States Patent
Onishi

(10) Patent No.: US 11,969,327 B2
(45) Date of Patent: Apr. 30, 2024

(54) ABSORBENT ARTICLE

(71) Applicant: UNICHARM CORPORATION, Ehime (JP)

(72) Inventor: Kazuaki Onishi, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 965 days.

(21) Appl. No.: 16/960,888

(22) PCT Filed: Dec. 20, 2018

(86) PCT No.: PCT/JP2018/047119
§ 371 (c)(1),
(2) Date: Jul. 9, 2020

(87) PCT Pub. No.: WO2019/138842
PCT Pub. Date: Jul. 18, 2019

(65) Prior Publication Data
US 2020/0337914 A1 Oct. 29, 2020

(30) Foreign Application Priority Data
Jan. 10, 2018 (JP) ................................. 2018-002254

(51) Int. Cl.
*A61F 13/537* (2006.01)
*A61F 13/49* (2006.01)
*A61F 13/53* (2006.01)

(52) U.S. Cl.
CPC ............ *A61F 13/537* (2013.01); *A61F 13/49* (2013.01); *A61F 2013/530481* (2013.01)

(58) Field of Classification Search
CPC .................... A61F 13/537; A61F 13/49; A61F 2013/530481
See application file for complete search history.

(56) References Cited

U.S. PATENT DOCUMENTS 5,998,695 A * 12/1999 Roe .......................... A61L 15/18
604/367
6,018,093 A * 1/2000 Roe .......................... A61L 15/18
604/367
(Continued)

FOREIGN PATENT DOCUMENTS

| CN | 103260570 A | 8/2013 |
| CN | 103957857 A | 7/2014 |

(Continued)

*Primary Examiner* — Guy K Townsend
(74) *Attorney, Agent, or Firm* — HAUPTMAN HAM, LLP

(57) ABSTRACT

In an absorbent article, an absorbent core includes first and second layers adjacent to each other in the thickness direction; the first layer has, in a front-body part, a groove extending in the longitudinal direction, penetrating in the thickness direction, and having a terminal end at a rear position and a base disposed adjacent to the rear position of the groove with the terminal end therebetween; the second layer has a groove corresponding part and a base corresponding part at positions overlapping the groove and the base respectively in the thickness direction; and the average density of highly absorbent polymer particles contained in the base and the average density of the highly absorbent polymer particles contained in the base corresponding part are higher than the average density of the highly absorbent polymer particles contained in the groove corresponding part.

15 Claims, 18 Drawing Sheets

(56) References Cited

U.S. PATENT DOCUMENTS

| | | | | |
|---|---|---|---|---|
| 6,372,952 | B1* | 4/2002 | Lash | A61F 13/53752 |
| | | | | 604/378 |
| 6,395,955 | B1* | 5/2002 | Roe | A61L 15/48 |
| | | | | 604/362 |
| 6,450,998 | B1* | 9/2002 | Otsubo | A61F 13/495 |
| | | | | 604/383 |
| 6,458,111 | B1* | 10/2002 | Onishi | A61F 13/495 |
| | | | | 604/385.01 |
| 6,551,295 | B1* | 4/2003 | Schmidt | A61F 13/5376 |
| | | | | 604/385.01 |
| 6,570,057 | B1* | 5/2003 | Schmidt | A61F 13/534 |
| | | | | 604/378 |
| 6,590,138 | B2* | 7/2003 | Onishi | A61F 13/532 |
| | | | | 604/383 |
| 6,626,880 | B2* | 9/2003 | Onishi | A61K 8/4966 |
| | | | | 604/383 |
| 6,664,439 | B1* | 12/2003 | Arndt | A61F 13/15203 |
| | | | | 604/374 |
| 6,720,471 | B1* | 4/2004 | Arndt | A61F 13/53747 |
| | | | | 604/378 |
| 6,869,423 | B2* | 3/2005 | Onishi | A61F 13/495 |
| | | | | 604/385.01 |
| 6,897,350 | B2* | 5/2005 | Yagou | A61F 13/512 |
| | | | | 604/378 |
| 7,378,567 | B2* | 5/2008 | Mangold | A61F 13/539 |
| | | | | 156/196 |
| 7,727,212 | B2* | 6/2010 | Sakai | A61F 13/539 |
| | | | | 604/383 |
| 7,772,455 | B1* | 8/2010 | Roe | A61F 13/51113 |
| | | | | 604/385.01 |
| 7,838,723 | B1* | 11/2010 | Schmidt | A61F 13/15203 |
| | | | | 604/385.01 |
| 8,556,875 | B2* | 10/2013 | Takahashi | A61F 13/535 |
| | | | | 604/385.101 |
| 8,927,803 | B2* | 1/2015 | Sakai | A61F 13/4756 |
| | | | | 604/385.101 |
| 10,675,188 | B2* | 6/2020 | Ludwig | A61F 13/49017 |
| 11,344,454 | B2* | 5/2022 | Ludwig | A61F 13/15203 |
| 11,399,992 | B2* | 8/2022 | Tally | A61F 13/64 |
| 11,452,646 | B2* | 9/2022 | Tally | A61F 13/4758 |
| 2001/0023339 | A1* | 9/2001 | Onishi | A61F 13/534 |
| | | | | 604/383 |
| 2001/0037103 | A1* | 11/2001 | Onishi | A61F 13/51121 |
| | | | | 604/385.19 |
| 2001/0053902 | A1* | 12/2001 | Roe | A61F 13/15 |
| | | | | 604/385.01 |
| 2002/0026168 | A1* | 2/2002 | Yagou | A61F 13/512 |
| | | | | 604/385.01 |
| 2002/0035354 | A1* | 3/2002 | Mirle | A61F 13/5146 |
| | | | | 604/385.01 |
| 2002/0091368 | A1* | 7/2002 | LaVon | A61F 13/15203 |
| | | | | 604/385.19 |
| 2002/0111594 | A1* | 8/2002 | Onishi | A61F 13/495 |
| | | | | 604/385.28 |
| 2003/0045851 | A1* | 3/2003 | Vartiainen | A61F 13/535 |
| | | | | 604/383 |
| 2006/0184151 | A1* | 8/2006 | Onishi | A61F 13/15203 |
| | | | | 604/385.24 |
| 2006/0287636 | A1* | 12/2006 | Sakai | A61F 13/532 |
| | | | | 604/385.101 |
| 2008/0103287 | A1* | 5/2008 | Chino | C08C 19/22 |
| | | | | 528/421 |
| 2011/0208147 | A1* | 8/2011 | Kawakami | A61F 13/5323 |
| | | | | 604/385.01 |
| 2012/0078209 | A1* | 3/2012 | Sakai | A61F 13/53 |
| | | | | 604/378 |
| 2012/0323195 | A1* | 12/2012 | Ehrnsperger | A61F 13/15 |
| | | | | 604/366 |
| 2013/0079740 | A1* | 3/2013 | Ehrnsperger | A61L 15/58 |
| | | | | 604/367 |
| 2013/0331806 | A1* | 12/2013 | Rosati | A61F 13/53743 |
| | | | | 604/366 |
| 2014/0005622 | A1* | 1/2014 | Wirtz | A61F 13/539 |
| | | | | 604/366 |
| 2014/0005623 | A1* | 1/2014 | Wirtz | A61F 13/53418 |
| | | | | 604/366 |
| 2014/0121487 | A1* | 5/2014 | Faybishenko | G16H 40/63 |
| | | | | 600/365 |
| 2015/0065981 | A1* | 3/2015 | Roe | A61F 13/4756 |
| | | | | 604/378 |
| 2015/0157251 | A1* | 6/2015 | Nelson | A61B 5/14507 |
| | | | | 600/580 |
| 2015/0282998 | A1* | 10/2015 | Arizti | A61F 13/51104 |
| | | | | 604/385.19 |
| 2017/0246052 | A1* | 8/2017 | Ludwig | A61F 13/15585 |
| 2017/0246056 | A1* | 8/2017 | Tagomori | A61F 13/47272 |
| 2017/0252015 | A1* | 9/2017 | Barnhorst | A61F 13/42 |
| 2018/0049929 | A1* | 2/2018 | Konawa | A61F 13/534 |
| 2018/0369029 | A1* | 12/2018 | Barnhorst | A61F 13/51456 |
| 2020/0337914 | A1* | 10/2020 | Onishi | A61F 13/539 |

FOREIGN PATENT DOCUMENTS

| | | | | |
|---|---|---|---|---|
| EP | 2679208 | A1 | 1/2014 | |
| JP | 201068954 | A | 4/2010 | |
| JP | 2010068954 | A * | 4/2010 | A61F 13/49 |
| JP | 2012-130365 | A | 7/2012 | |
| JP | 201649199 | A | 4/2016 | |
| JP | 2016168300 | A | 9/2016 | |
| WO | 2012086265 | A1 | 6/2012 | |
| WO | 2013187375 | A1 | 12/2013 | |

* cited by examiner

ABSORBENT ARTICLE

RELATED APPLICATIONS

The present application is a National Phase of International Application Number PCT/JP2018/047119, filed Dec. 20, 2018, and claims priority to Japanese Application number 2018-002254, filed Jan. 10, 2018.

FIELD

The present invention relates to an absorbent article.

BACKGROUND

Various improvements have been made in order to realize preferable wearing comfort while preventing leakage of excrement such as urine, etc.

For example, in Patent Literature 1, an absorbent article is disclosed which includes a top sheet that is arranged on the skin contact surface side, a back sheet that is arranged on the skin non-contact surface side, and an absorbent body that is arranged between both sheets, wherein the absorbent body has a longitudinal direction and a width direction which is orthogonal thereto, the absorbent body has a protruded absorption portion which is discontinuously scattered in the plane direction on the skin non-contact surface side in the excretory portion corresponding region, and a liquid flow structure which is disposed in each of the longitudinal direction and the width direction between the protruded absorption portion, the liquid flow structure is configured by a groove-like recess portion which is recessed in the thickness direction from the skin non-contact surface side of the absorbent body and a recess portion absorption portion which is positioned at a bottom portion on the skin contact surface side of the recess portion, the density of the recess portion absorption portion is smaller than the density of the protruded absorption portion, and the protruded absorption portion has an area of a surface at a lower portion on the skin non-contact surface side which is larger than an area of a surface at an upper portion on the skin contact surface side. Further, in Patent Literature 1, a disposable diaper is mentioned as an example of the absorbent article.

CITATION LIST

Patent Literature

[PTL 1] Japanese Unexamined Patent Publication No. 2012-130365

SUMMARY

Technical Problem

In the absorbent article described in Patent Literature 1, the recess portion absorption portion which forms the liquid flow structure is formed across the entirety of the longitudinal direction, whereby has a structure in which it is easy to make the body fluid supplied in spots move in the longitudinal direction of the absorbent body, and to make the absorbent body absorb the body fluid by using the entirety thereof.

However, in the absorbent article described in Patent Literature 1, when a large amount of body fluid such as urine, etc., is supplied in spots, the body fluid moves rapidly to the rear side in the longitudinal direction of the absorbent article by passing through the recess portion absorption portion which extends in the longitudinal direction, and further, the body fluid which can no longer be stored in the recess portion absorption portion flows on the surface of the top sheet so as to move to the rear side in the longitudinal direction of the absorbent article, whereby there may be cases in which the leakage occurs in the crotch region, etc.

Accordingly, the object of the present disclosure is to provide an absorbent article in which it is easy to make the body fluid flow in the longitudinal direction of the absorbent core and it is difficult for the leakage to occur in the crotch region.

Solution to Problem

The inventors of the present disclosure has found out that an absorbent article which includes an absorbent core that has superabsorbent polymers, wherein the absorbent article includes a longitudinal direction that has a front side and a rear side, a width direction, and a thickness direction, and is partitioned into a front body and a rear body, the absorbent core includes a first layer and a second layer which are adjacent to each other in the thickness direction, the first layer includes (i) a groove portion which extends along the longitudinal direction, penetrates in the thickness direction, and includes a terminal edge at a position on the rear side, and (ii) a base portion which is arranged adjacent to the position on the rear side of the groove portion with the terminal edge placed in between, the groove portion and the base portion being arranged at the front body, the second layer includes a groove portion corresponding portion and a base portion corresponding portion at positions which overlap with the groove portion and the base portion in the thickness direction, respectively, and each of an average density of the superabsorbent polymers included in the base portion and an average density of the superabsorbent polymers included in the base portion corresponding portion is larger than an average density of the superabsorbent polymers included in the groove portion corresponding portion, is the solution to the problem.

Advantageous Effects of Invention

According to the absorbent article of the present disclosure, it is easy to make the body fluid flow in the longitudinal direction of the absorbent core and it is difficult for the leakage to occur in the crotch region.

DESCRIPTION OF EMBODIMENTS

Definitions

"In a Plan View"

Figure 1:
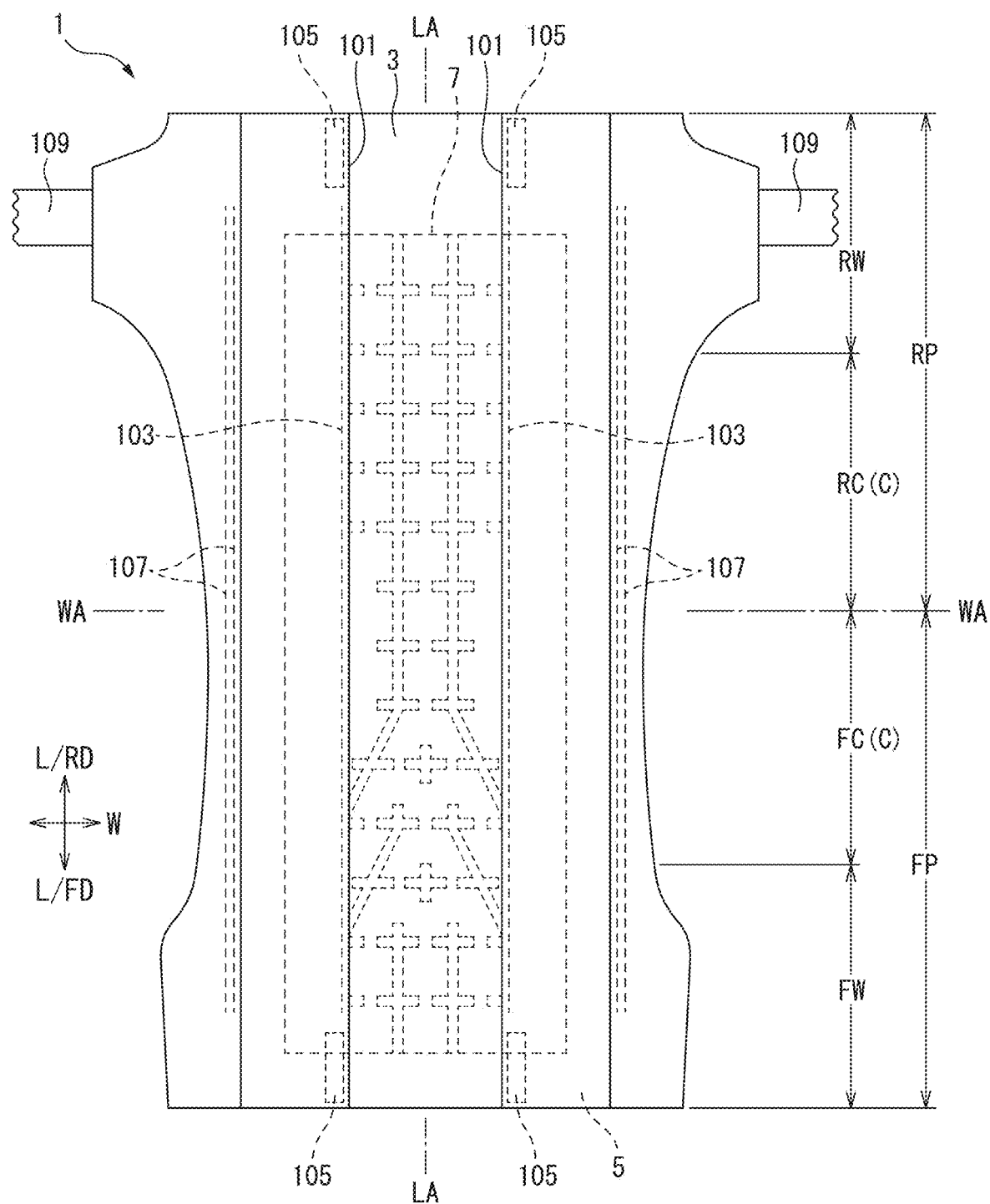
FIG. 1 is a plan view of the absorbent article 1 according to the first embodiment.

In the present description, unless otherwise particularly noted, "in a plan view" means "viewing an object (for example, an absorbent article, an absorbent body, and an absorbent core, etc.) which is placed on a horizontal plane in a state of being expanded, from an upper side or a lower side in the thickness direction thereof". In particular, in a case in which the object is an absorbent article, viewing the absorbent article in a state of being expanded in the thickness direction from the top sheet side may simply be referred to as "in a plan view", and in a case in which the object is an absorbent core, viewing the absorbent article in a state of being expanded in the thickness direction may simply be referred to as "in a plan view".

"The Longitudinal Direction", "the Width Direction", and "the Thickness Direction"

In the present description, "the longitudinal direction" is referred to as "the longer direction of the lengths of a longitudinal object in a plan view", "the width direction" is referred to as "the shorter direction of the lengths of a longitudinal object in a plan view", and "the thickness direction" is referred to as "the vertical direction with respect to an object which is placed on a horizontal plane in a state of being expanded". These longitudinal direction, width direction, and thickness direction are in a relationship of being mutually orthogonal to each other.

Incidentally, in the present description, in a case in which "the longitudinal direction", "the width direction", and "the thickness direction" are simply mentioned, they mean "the longitudinal direction", "the width direction", and "the thickness direction" of an absorbent article, respectively.

"The Longitudinal Direction Axis Line" and "the Width Direction Axis Line"

In the present description, "the longitudinal direction axis line" means the axis line which extends in the longitudinal direction at the center of the width direction of an absorbent article. Further, in the present description, "the width direction axis line" means the axis line which extends in the width direction at the center of the longitudinal direction of an absorbent article.

Incidentally, in the present description, in a case in which "the longitudinal direction axis line" and "the width direction axis line" are simply mentioned, they mean "the longitudinal direction axis line" and "the width direction axis line" of an absorbent article, respectively.

"The Front Side" and "the Rear Side"

In the present description, "the front side" and "the rear side" means the direction on the front surface side and the direction on the back surface side of the wearer in the longitudinal direction, respectively.

"The Skin Facing Surface (Side)" and "the Skin Non-Facing Surface (Side)"

In the present description, "the skin facing surface (side)" means, in the thickness direction of an absorbent article, "the relatively closer side with respective to the skin facing surface of the wearer at the time of wearing the absorbent article", and "the skin non-facing surface (side)" means "the relatively farther side with respective to the skin facing surface of the wearer at the time of wearing the absorbent article".

Further, in the present description, "the skin facing surface" and "the skin non-facing surface" means "the surface on the skin facing surface side" and "the surface on the skin non-facing surface side" of various members which configure an absorbent article (such as, the top sheet, the absorbent body, and the back sheet, etc.), respectively.

"The Front Body" and "the Rear Body"

In the present description, "the front body" and "the rear body" are partitioned sections of an absorbent article, and "the front body" and "the rear body" mean the region on the front side and the region on the rear side with respect to the width direction axis line of the absorbent article, respectively.

"The Front Waist Region", "the Rear Waist Region", and "the Crotch Region (the Front Crotch Region and the Rear Crotch Region)"

In the present description, "the front waist region", "the rear waist region", and "the crotch region (the front crotch region and the rear crotch region)" are terms which are used in a case in which the absorbent article is a disposable diaper, and the meanings are as follows.

In a pants type disposable diaper, the front waist region means the region which is sandwiched by a pair of joining portions that join the front body and the rear body in the front body, and the rear waist region means the region which is sandwiched by the pair of joining portions in the rear body.

Further, in a pants type disposable diaper, the crotch region means the region between the front waist region and the rear waist region in a plan view of the pants type disposable diaper. Further, the crotch region corresponds to the region which is sandwiched by the pair of leg opening portions 117 (refer to FIG. 14).

Figure 14:
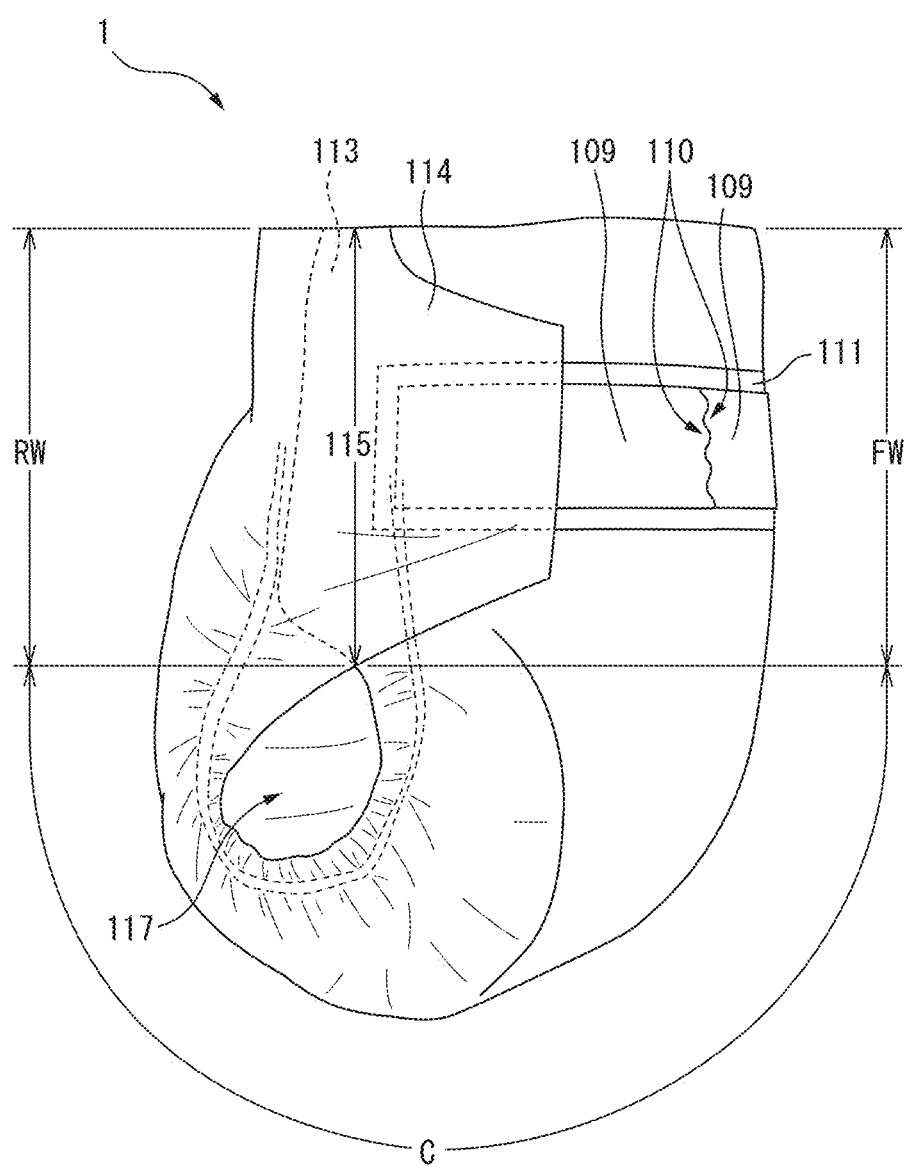
FIG. 14 is a diagram so as to explain the front waist region FW, the rear waist region RW, and the crotch region C of a tape type disposable diaper.

In a tape type disposable diaper, as shown in FIG. 14, the front waist region FW, the rear waist region RW, and the crotch region C are partitioned in a state in which the tips 110 of the pair of tape fastener 109 are fixed so as to be adjacent to each other to the fixed region for tape fastener 111.

To be specific, the waist regions (FW+RW) are judged based on the pair of overlapped portions 115 in which the waist formation member 113 of the front body and the waist formation member 114 of the rear body overlap with each other in the absorbent article 1, in a state of being fixed in the above-mentioned manner. The front waist region FW means the region between the pair of overlapped portions 115 in the front body of the absorbent article 1. In the same manner, the rear waist region RW means the region between the pair of overlapped portions 115 in the rear body of the absorbent article 1. The crotch region C means the region between the front waist region FW and the rear waist region RW.

Incidentally, the crotch region is partitioned into "the front crotch region" which is present in the front body, and "the rear crotch region" which is present in the rear body.

In the present description, "the groove portion" means the groove portion which extends along the longitudinal direction, and the groove portion is arranged so that an axis line of the groove portion has an angle of preferably less than 45°, more preferably less than 30°, and even more preferably less than 15°, with respect to the longitudinal axis line at an arbitrary position. When the angle is 45° or more, it becomes difficult for the body fluid which is present in the groove portion to flow in the longitudinal direction of the absorbent core.

In the present description, the width of the groove portion means the length of the groove portion in the direction which is orthogonal to the axis line of the groove portion.

In the present description, "the subordinate groove portion" means the groove portion which is present in a connected manner through the base edge of the groove portion with a predetermined interval in the direction which intersects with the above-mentioned groove portion. The subordinate groove portion is arranged so that an axis line of the subordinate groove portion has an angle of preferably 45° or more, more preferably 60° or more, and even more preferably 80° or more, with respect to the axis line of the groove portion at the portion which is connected to the groove portion (that is, the base edge). The subordinate groove portion may be extended in a linear manner, or in a non-linear manner, such as a curved manner.

In the present description, the width of the subordinate groove portion means the length of the subordinate groove portion in the direction which is orthogonal to the axis line of the subordinate groove portion.

Specifically, the present disclosure relates to the following aspects.

[Aspect 1]

An absorbent article which includes an absorbent core that has superabsorbent polymers, wherein the absorbent article includes a longitudinal direction that has a front side and a rear side, a width direction, and a thickness direction, and is partitioned into a front body and a rear body, the absorbent core includes a first layer and a second layer which are adjacent to each other in the thickness direction, the first layer includes (i) a groove portion which extends along the longitudinal direction, penetrates in the thickness direction, and includes a terminal edge at a position on the rear side, and (ii) a base portion which is arranged adjacent to the position on the rear side of the groove portion with the terminal edge placed in between, the groove portion and the base portion being arranged at the front body, the second layer includes a groove portion corresponding portion and a base portion corresponding portion at positions which overlap with the groove portion and the base portion in the thickness direction, respectively, and each of an average density of the superabsorbent polymers included in the base portion and an average density of the superabsorbent polymers included in the base portion corresponding portion is larger than an average density of the superabsorbent polymers included in the groove portion corresponding portion.

Generally, in an absorbent article which absorbs body fluid with a relatively large amount, such as urine, etc., in order to make the entire absorbent core absorb the body fluid which is supplied in spots, the design is made so as to make the body fluid move in the longitudinal direction of the absorbent core. As one example of such design, the groove portion which is arranged in the longitudinal direction of the absorbent core may be mentioned.

However, when a large amount of body fluid is supplied at once in spots to such an absorbent article, the body fluid which can no longer be absorbed by the absorbent core flows to the rear side of the absorbent article at once by passing through the surface of the absorbent article (the surface of the liquid permeable sheet), whereby there may be cases in which the leakage occurs in the crotch region.

The above-mentioned absorbent article includes the predetermined groove portion, the base portion, the groove portion corresponding portion, and the base portion corresponding portion, and further, each of the average density of the superabsorbent polymers included in the base portion and the average density of the superabsorbent polymers included in the base portion corresponding portion is larger than the average density of the superabsorbent polymers included in the groove portion corresponding portion.

Hereinbelow, the flow velocity of the body fluid which flows toward the rear side on the surface of the absorbent article is referred to as "the surface flow velocity". Further, the average flow velocity of the body fluid which flows to the rear side by passing through the first layer is referred to as "the first layer average flow velocity", the flow velocity of the body fluid which flows to the rear side by passing through the groove portion of the first layer is referred to as "the first layer groove portion flow velocity", and the flow velocity of the body fluid which flows to the rear side by passing through the base portion of the first layer is referred to as "the first layer base portion flow velocity". Still further, the average flow velocity of the body fluid which flows to the rear side by passing through the second layer is referred to as "the second layer average flow velocity", the flow velocity of the body fluid which flows to the rear side by passing through the groove portion corresponding portion of the second layer is referred to as "the second layer groove portion corresponding portion flow velocity", and the flow velocity of the body fluid which flows to the rear side by passing through the base portion corresponding portion of the second layer is referred to as "the second layer base portion corresponding portion flow velocity".

In a case in which the first layer and the second layer are arranged on the skin side and the clothing side, respectively, the groove portion in which the density of the material is low can receive the body fluid, and can make the received body fluid move to the rear side in the first groove portion flow velocity. Further, the groove portion can deliver the body fluid which is received by the groove portion to the groove portion corresponding portion of the second layer in which the average density of the superabsorbent polymers is relatively smaller. In the groove portion corresponding portion of the second layer, the body fluid can be made to move to the rear side in the second layer groove portion corresponding portion flow velocity which is slower than the first layer groove portion flow velocity.

As described above, in the surface flow velocity, the first layer groove portion flow velocity, and the second layer groove portion corresponding portion flow velocity, the following first relationship formula is established.

the surface flow velocity>the first layer groove portion flow velocity>the second layer groove portion corresponding portion flow velocity Further, in the above-mentioned absorbent article, at the rear side of the groove portion of the first layer, the base portion in which the average density of the superabsorbent polymers is relatively larger than the groove portion is present, whereby the base portion once blocks the body fluid which is present in the groove portion, the superabsorbent polymers which are present in the base portion make the body fluid which is present in the groove portion permeate to the rear side in the first layer base portion flow velocity, and partially absorb the body fluid which is present in the groove portion. Further, at the rear side of the groove portion corresponding portion of the second layer, the base portion corresponding portion in which the average density of the superabsorbent polymers is relatively larger than the groove portion corresponding portion is present, whereby the base portion corresponding portion once blocks the body fluid which is present in the groove portion corresponding portion, makes the body fluid which is present in the groove portion corresponding portion permeate to the rear side in the second layer base portion corresponding portion flow velocity, and the superabsorbent polymers which are present in the base portion corresponding portion partially absorb the body fluid which is present in the groove portion corresponding portion.

In the surface flow velocity, the first layer base portion flow velocity, and the second layer base portion corresponding portion flow velocity, the following second relationship formula is established.

the surface flow velocity>the first layer base portion flow velocity, the second layer base portion corresponding portion flow velocity As described above, in the surface flow velocity, the first layer average flow velocity, and the second layer average flow velocity, the following third relationship formula is established, the surface flow velocity>the first layer average flow velocity>the second layer average flow velocity and the body fluid can be made to move to the rear side of the absorbent core step by step.

Further, in a case in which the first layer and the second layer are arranged on the clothing side and the skin side, respectively, other than making the body fluid move to the groove portion of the first layer after making the same permeate through the groove portion corresponding portion of the second layer, the relationship of the first formula, the second formula and the third formula is satisfied, whereby body fluid can be made to move to the rear side of the absorbent core step by step. Still further, since the body fluid can be locked in the groove portion of the first layer, even in a case in which the wearer moves, it is difficult for the leakage to occur in the crotch region (especially in the rear crotch region which is often at the lowest position when being worn).

As described above, according to the above-mentioned absorbent article, it is easy to make the body fluid flow in the longitudinal direction of the absorbent core and it is difficult for the leakage to occur in the crotch region (especially in the rear crotch region).

[Aspect 2]

The absorbent article according to aspect 1, wherein the average density of the superabsorbent polymers included in the base portion corresponding portion is larger than the average density of the superabsorbent polymers included in the base portion.

In the above-mentioned absorbent article, the average density of the superabsorbent polymers included in the base portion corresponding portion of the second layer is larger than the average density of the superabsorbent polymers included in the base portion of the first layer, whereby in a case in which the body fluid is absorbed repeatedly, in the first layer base portion flow velocity and the second layer base portion corresponding portion flow velocity, the following fourth relationship formula is established, the first layer base portion flow velocity>the second layer base portion corresponding portion flow velocity and the difference between the first layer average flow velocity and the second layer average flow velocity can be made to be larger.

Therefore, according to the above-mentioned absorbent article, it is easy to make the body fluid flow in the longitudinal direction of the absorbent core and it is difficult for the leakage to occur in the crotch region (especially in the rear crotch region).

[Aspect 3]

The absorbent article according to aspect 1 or 2, wherein the groove portion extends in a direction which intersects with the longitudinal direction.

In the above-mentioned absorbent article, the groove portion extends in the direction which intersects with the longitudinal direction, whereby the route between the groove portion of the first layer and the groove portion corresponding portion of the second layer can be made to be longer, and the first layer groove portion flow velocity and the second layer groove portion corresponding portion flow velocity can be made to be slower, and thus the differences between the surface flow velocity and each of the first layer average flow velocity and the second layer average flow velocity can be made to be larger.

Therefore, according to the above-mentioned absorbent article, it is easy to make the body fluid flow in the longitudinal direction of the absorbent core and it is difficult for the leakage to occur in the crotch region (especially in the rear crotch region).

[Aspect 4]

The absorbent article according to any one of aspects 1 to 3, wherein the groove portion is arranged toward the rear side so as to approach a longitudinal direction axis line of the absorbent article.

In the above-mentioned absorbent article, the groove portion is arranged toward the rear side so as to approach the longitudinal direction axis line of the absorbent core, whereby the differences between the surface flow velocity and each of the first layer average flow velocity and the second layer average flow velocity can be made to be larger, and the body fluid can be made to move toward the rear side so as to approach the longitudinal direction axis line of the absorbent core, that is, the center in the width direction of the absorbent core.

Therefore, according to the above-mentioned absorbent article, it is easy to make the body fluid flow in the longitudinal direction of the absorbent core and it is difficult for the leakage to occur in the crotch region (especially in the rear crotch region).

[Aspect 5]

The absorbent article according to any one of aspects 1 to 4, wherein the first layer further includes a pair of width direction base portions which are arranged adjacent to both sides in the width direction of the groove portion, the second layer further includes a pair of width direction base portion corresponding portions which are arranged at positions which overlap with the pair of width direction base portions in the thickness direction, and each of an average density of the superabsorbent polymers included in each of the pair of width direction base portions and the average density of the superabsorbent polymers included in the groove portion corresponding portion is smaller than an average density of the superabsorbent polymers included in each of the pair of width direction base portion corresponding portions.

In the above-mentioned absorbent article, the body fluid which has been blocked by the base portion and kept in the groove portion is absorbed by the pair of width direction base portions which include the superabsorbent polymers, and subsequently, the body fluid which can no longer be retained by the pair of width direction base portions can be absorbed and retained by the pair of width direction base portion corresponding portions which have a higher average density of the superabsorbent polymers than each of the pair of width direction base portions.

Further, each of the groove portion corresponding portion, the width direction base portion, and the width direction base portion corresponding portion includes a predetermined amount of superabsorbent polymers, and the swelling of the width direction base portion and the groove portion corresponding portion which is present in the surrounding of the groove portion is suppressed, whereby it is easy to maintain the length in the width direction and the height in the thickness direction of the groove portion, and to secure the water flow function of the groove portion. As a result, according to the above-mentioned absorbent article, it is easy to make the body fluid flow in the longitudinal direction of the absorbent core and it is difficult for the leakage to occur in the crotch region (especially in the rear crotch region).

[Aspect 6]

The absorbent article according to aspect 5, wherein the average density of the superabsorbent polymers included in the groove portion corresponding portion is smaller than the average density of the superabsorbent polymers included in each of the pair of width direction base portions.

In the above-mentioned absorbent article, the average density of the superabsorbent polymers included in the groove portion corresponding portion is smaller than the average density of the superabsorbent polymers included in each of the pair of width direction base portions, whereby even in a case in which the body fluid is absorbed repeatedly, the swelling of the groove portion corresponding portion is suppressed, and it is difficult for the action of the groove portion corresponding portion making the body fluid move to the rear side and the action thereof making the body fluid permeate in the thickness direction (especially in a case in which the first layer is arranged on the clothing side) to be inhibited. Therefore, according to the above-mentioned absorbent article, it is easy to make the body fluid flow in the longitudinal direction of the absorbent core and it is difficult for the leakage to occur in the crotch region (especially in the rear crotch region).

[Aspect 7]

The absorbent article according to aspect 5 or 6, wherein the groove portion further includes a subordinate groove portion which penetrates in the thickness direction of the first layer, in a direction which intersects with the groove portion, and is present so as to be connected to the groove portion through a subordinate groove portion base edge.

In the above-mentioned absorbent article, the groove portion includes the predetermined subordinate groove portion. By regarding the subordinate groove portion as a portion of the groove portion, the presence of the subordinate groove portion can increase the amount of body fluid which can be received by the groove portion until the body fluid is blocked by the base portion, increase the surface area of the groove portion, and as a result, can reduce the amount of body fluid which flows toward the rear side on the surface of the absorbent article. Therefore, according to the above-mentioned absorbent article, it is easy to make the body fluid flow in the longitudinal direction of the absorbent core and it is difficult for the leakage to occur in the crotch region (especially in the rear crotch region).

[Aspect 8]

The absorbent article according to aspect 7, wherein the subordinate groove portion includes a subordinate groove portion terminal edge on an opposite side of the subordinate groove portion base edge.

In the above-mentioned absorbent article, the subordinate groove portion includes the subordinate groove portion terminal edge, whereby the body fluid which has been received by the subordinate groove portion does not move to the adjacent groove portion, etc., and thus it is difficult for the body fluid to move in the width direction of the absorbent core in which the length is short. Therefore, according to the above-mentioned absorbent article, it is easy to make the body fluid flow in the longitudinal direction of the absorbent core and it is difficult for the leakage to occur in the crotch region (especially in the rear crotch region).

[Aspect 9]

The absorbent article according to aspect 7 or 8, wherein the second layer further includes a subordinate groove portion corresponding portion which is arranged at a position which overlaps with the subordinate groove portion in the thickness direction, and an average density of the superabsorbent polymers included in the subordinate groove portion corresponding portion is smaller than the average density of the superabsorbent polymers included in each of the pair of width direction base portion corresponding portions.

In the above-mentioned absorbent article, the average density of the superabsorbent polymers included in the subordinate groove portion corresponding portion is smaller than the average density of the superabsorbent polymers included in each of the pair of width direction base portion corresponding portions, whereby it is easier for the subordinate groove portion corresponding portion to have the same action as the groove portion corresponding portion. Therefore, according to the above-mentioned absorbent article, it is easy to make the body fluid flow in the longitudinal direction of the absorbent core and it is difficult for the leakage to occur in the crotch region (especially in the rear crotch region).

[Aspect 10]

The absorbent article according to aspect 9, wherein the average density of the superabsorbent polymers included in the subordinate groove portion corresponding portion is smaller than the average density of the superabsorbent polymers included in each of the pair of width direction base portions.

In the above-mentioned absorbent article, the average density of the superabsorbent polymers included in the subordinate groove portion corresponding portion is smaller than the average density of the superabsorbent polymers included in each of the pair of width direction base portions, whereby it is easier for the subordinate groove portion corresponding portion to have the same action as the groove portion corresponding portion. Therefore, according to the above-mentioned absorbent article, it is easy to make the body fluid flow in the longitudinal direction of the absorbent core and it is difficult for the leakage to occur in the crotch region (especially in the rear crotch region).

[Aspect 11]

The absorbent article according to any one of aspects 1 to 10, wherein the first layer is arranged on a clothing side with respect to the second layer.

In the above-mentioned absorbent article, the first layer is arranged on the clothing side with respect to the second layer, whereby the body fluid can be locked in the groove portion of the first layer, and thus even in a case in which the wearer moves, it is difficult for the leakage to occur in the crotch region (especially in the rear crotch region).

[Aspect 12]

The absorbent article according to any one of aspects 1 to 11, wherein the absorbent article further includes a core wrap which is arranged in the first layer on a surface on an opposite side of the second layer, and the core wrap is arranged so as to protrude toward the second layer in the groove portion.

The above-mentioned absorbent article includes, in the groove portion, the core wrap which is arranged so as to be convex on the skin facing surface side, whereby the diffusion property of the body fluid in the groove portion can be improved.

Hereinbelow, the absorbent article according to the present disclosure is explained in detail.

Figure 2:
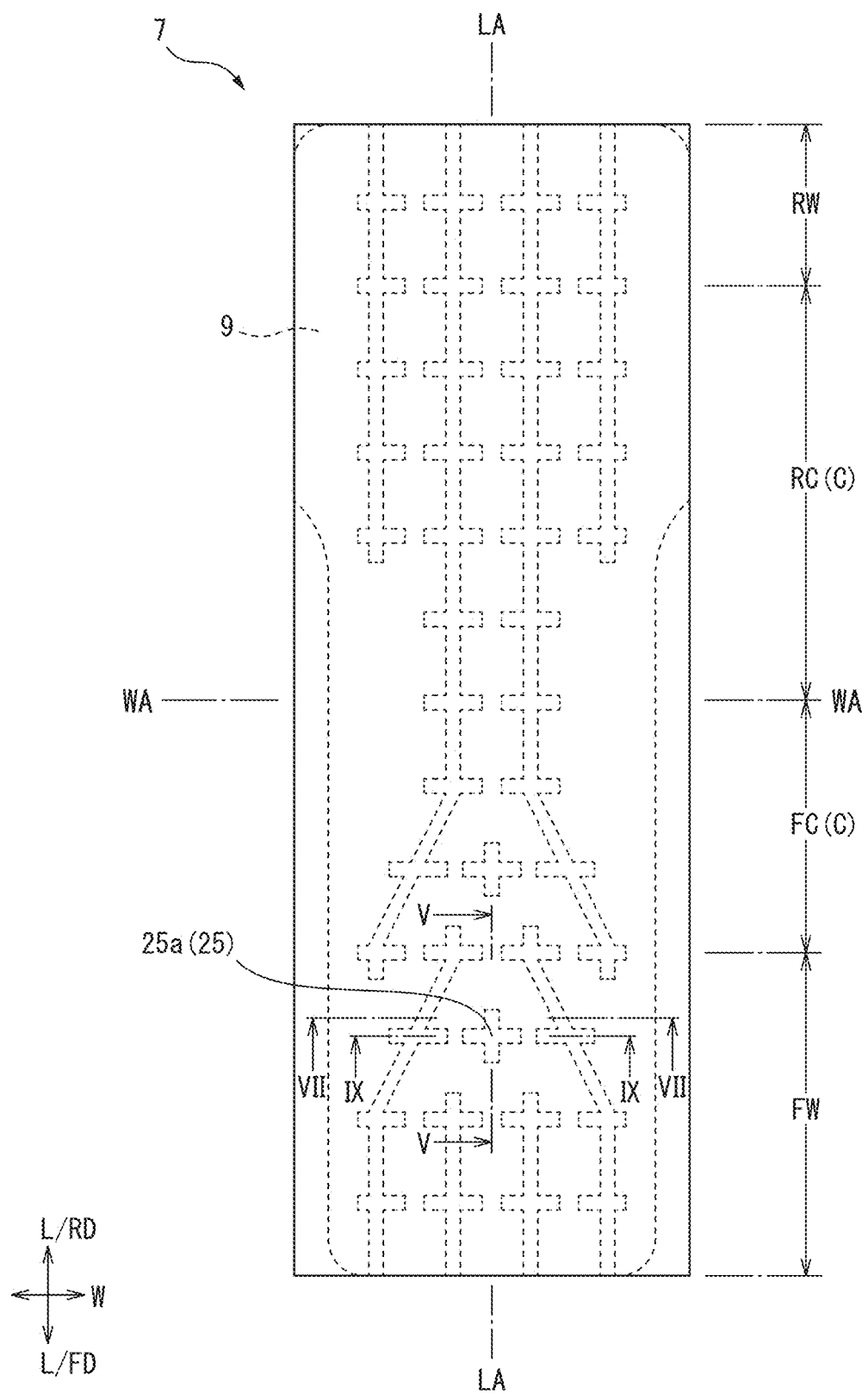
FIG. 2 is a plan view of the absorbent body 7 of the absorbent article 1.
Figure 3:
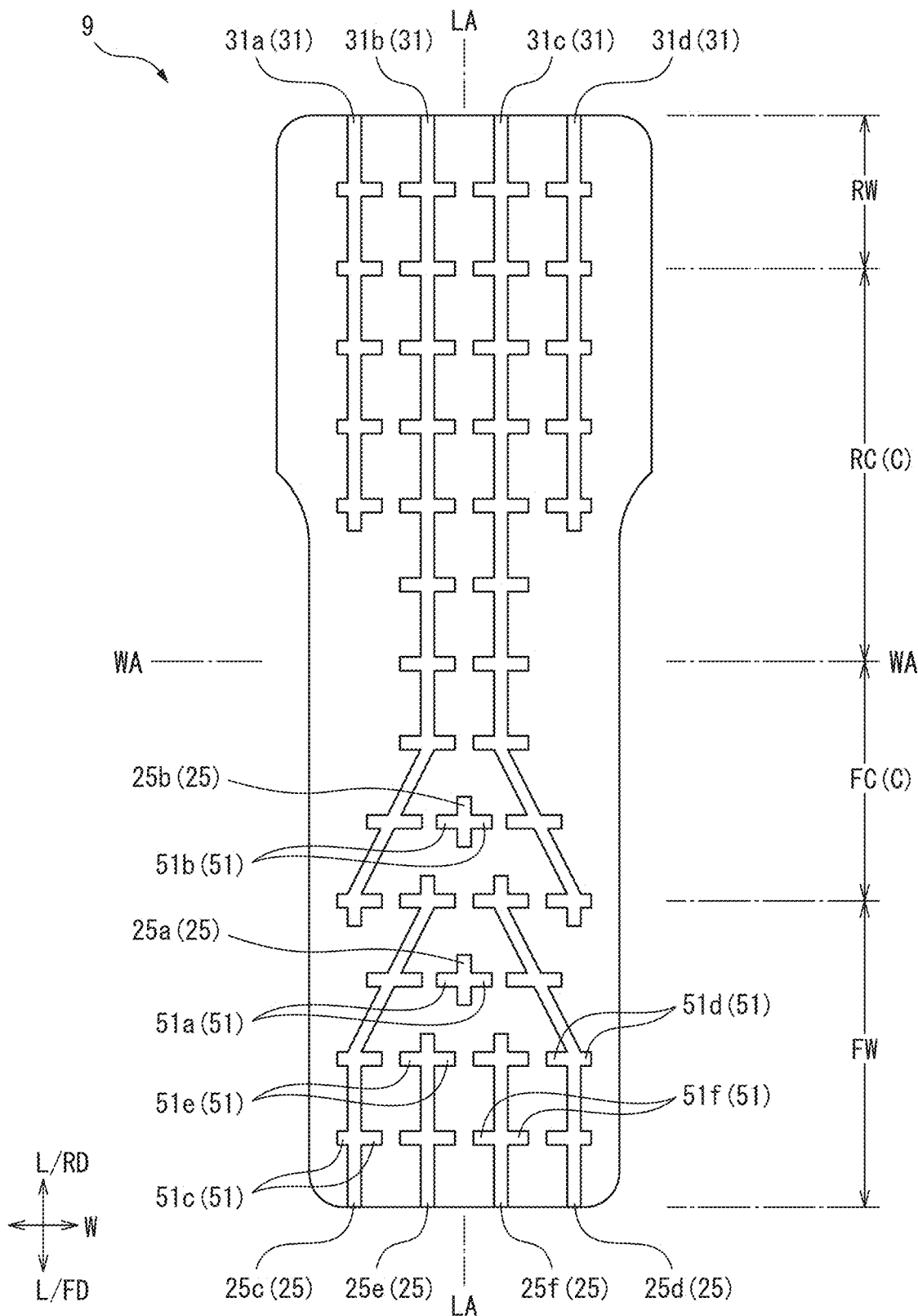
FIG. 3 is a plan view of the absorbent core 9 of the absorbent article 1.
Figure 4:
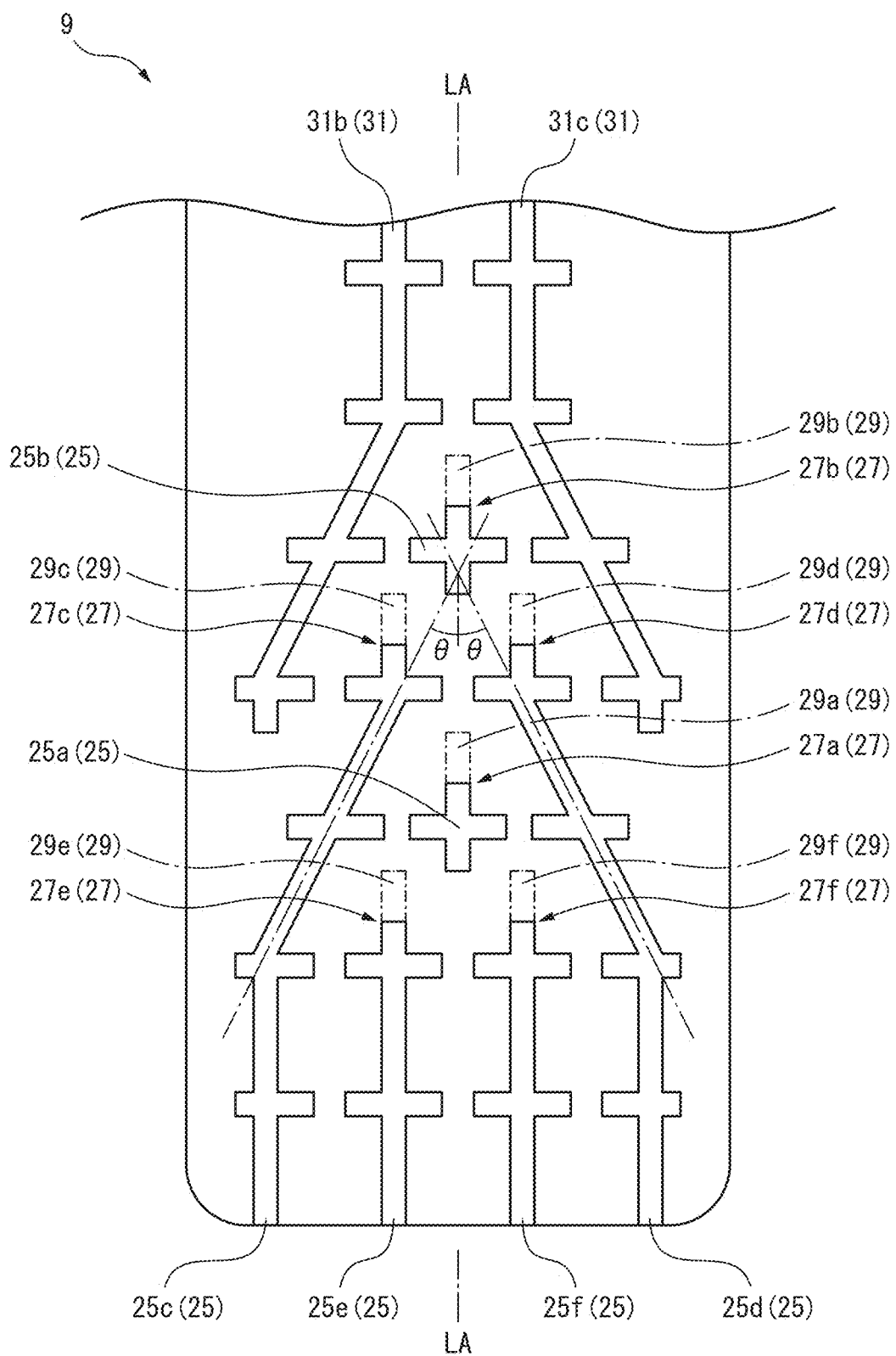
FIG. 4 is a partial enlarged view of the absorbent core 9.
Figure 5:
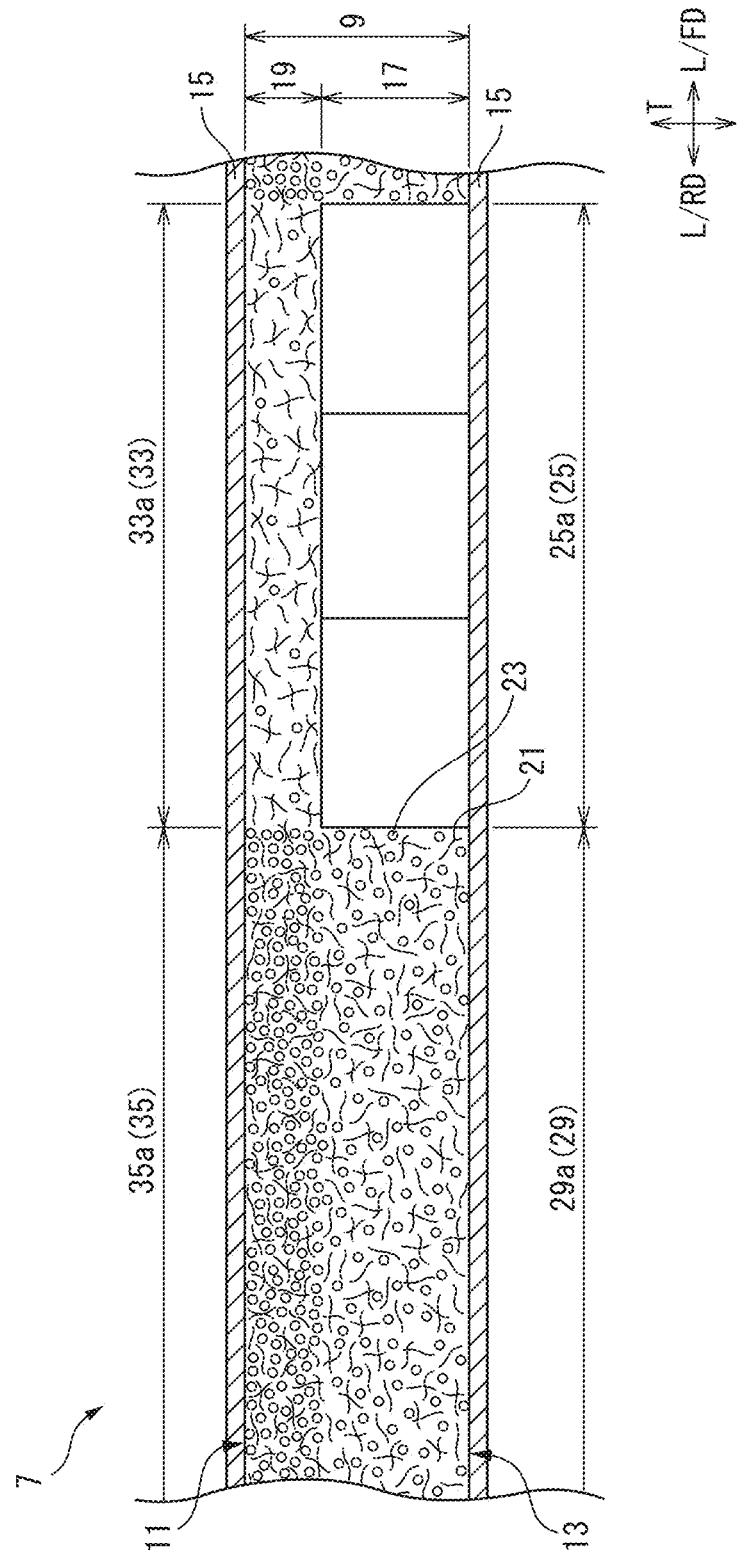
FIG. 5 is a cross sectional view at the V-V cross section of FIG. 2.
Figure 6:
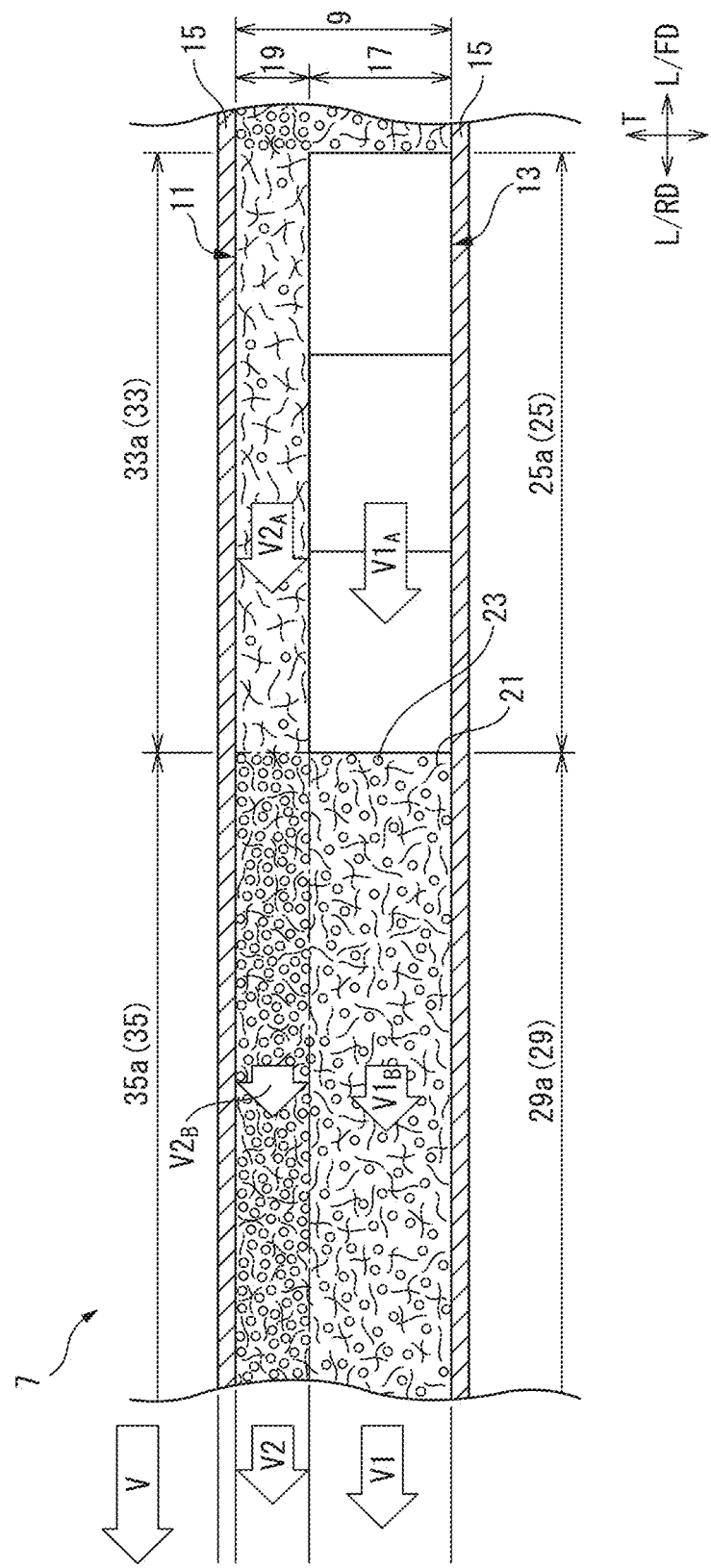
FIG. 6 is a cross sectional schematic view which shows the flow of the body fluid in the longitudinal direction L of the absorbent article 1.
Figure 7:
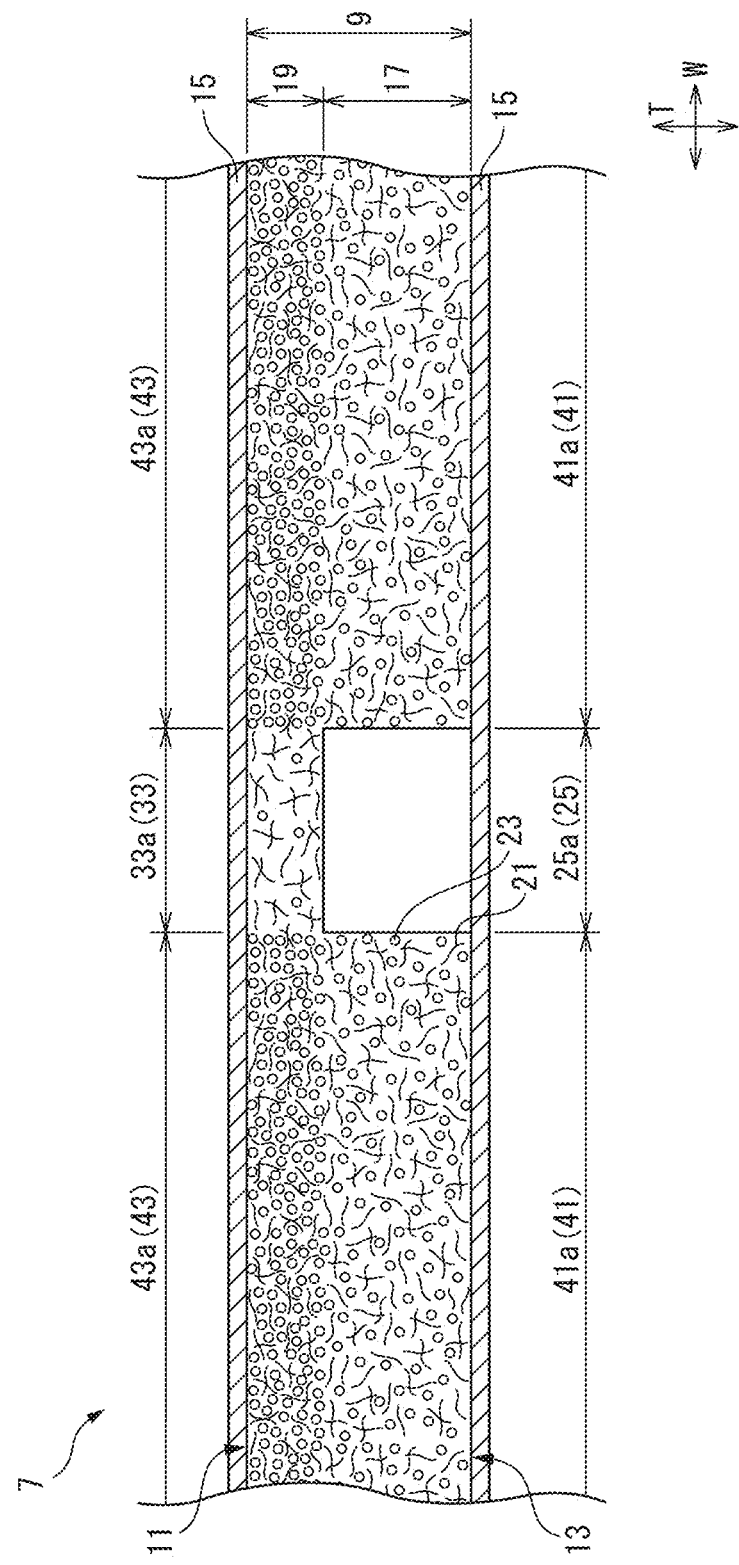
FIG. 7 is a cross sectional view at the VII-VII cross section of FIG. 2.
Figure 8:
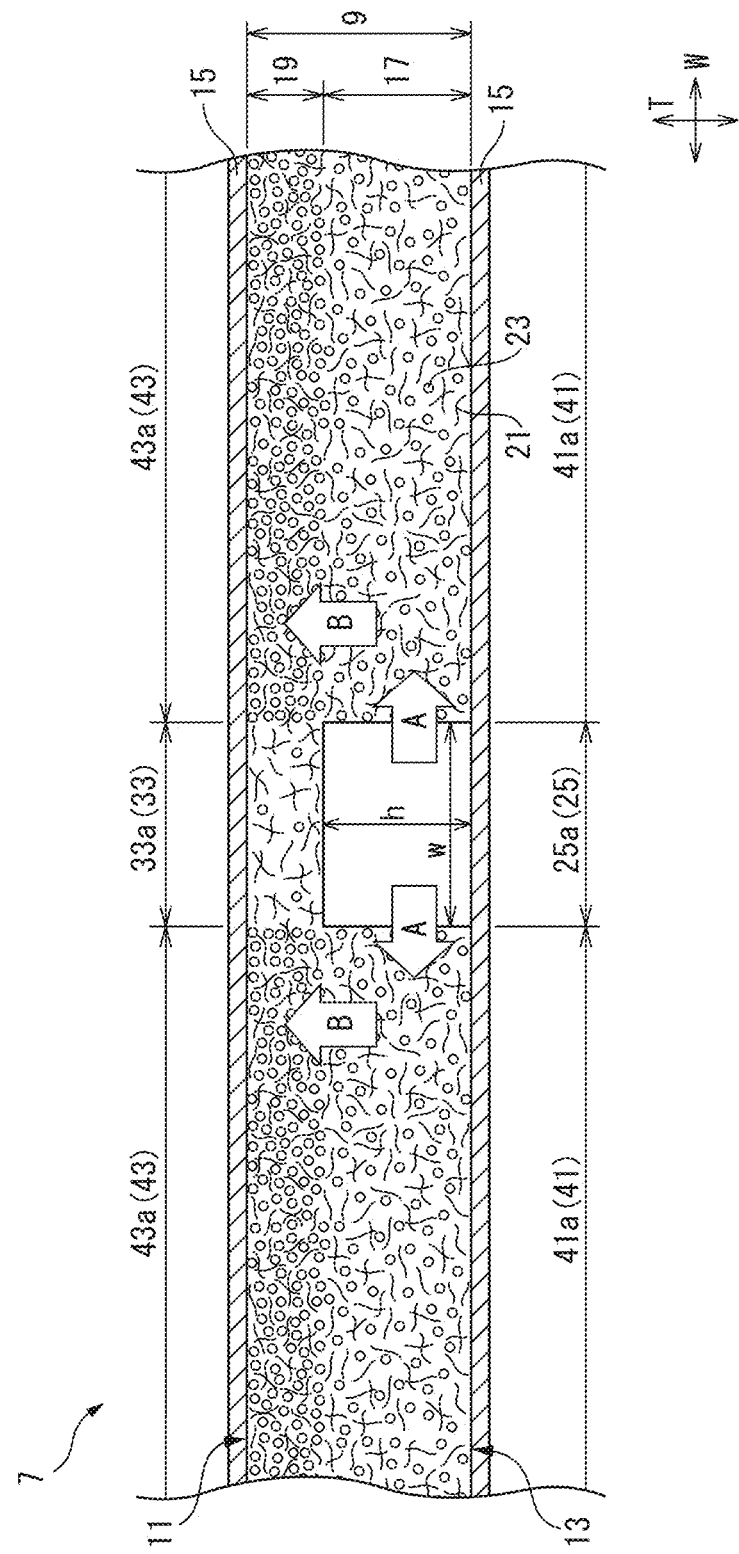
FIG. 8 is a cross sectional schematic view which shows the flow of the body fluid in the width direction W of the absorbent article 1.
Figure 9:
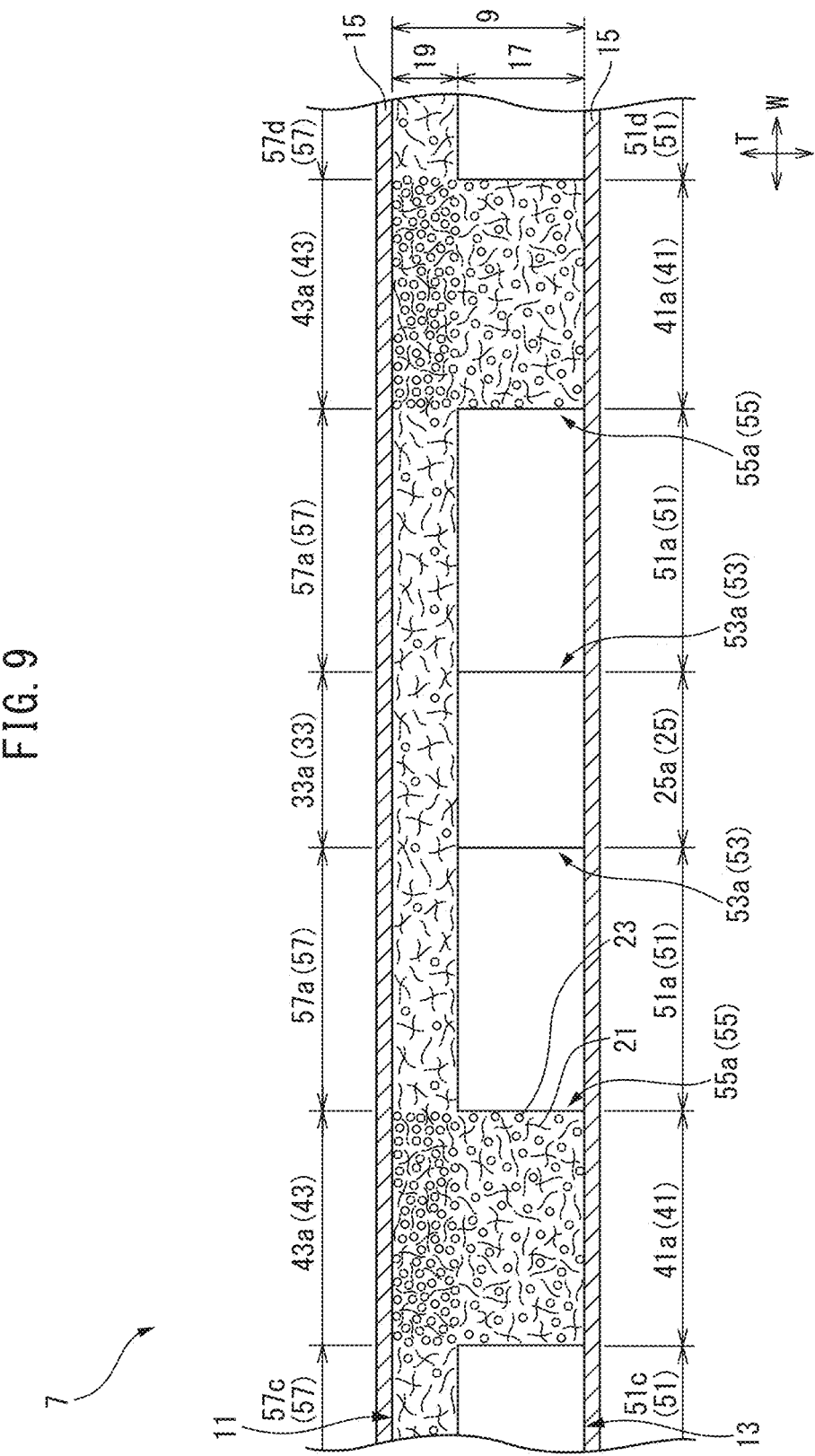
FIG. 9 is a cross sectional view at the IX-IX cross section of FIG. 2.

FIGS. 1 to 9 are diagrams so as to explain the absorbent article 1 according to one embodiment of the present disclosure (hereinbelow, which may be referred to as "the first embodiment"), and to be specific, a disposable diaper. Specifically, FIG. 1 is a plan view of the absorbent article 1. FIG. 2 is a plan view of the absorbent body 7 of the absorbent article 1. FIG. 3 is a plan view of the absorbent core 9 of the absorbent article 1. FIG. 4 is a partial enlarged view of the absorbent core 9. FIG. 5 is a cross sectional view at the V-V cross section of FIG. 2. FIG. 6 is a cross sectional schematic view which shows the flow of the body fluid in the longitudinal direction L of the absorbent article 1, and corresponds to the V-V cross section of FIG. 2. FIG. 7 is a cross sectional view at the VII-VII cross section of FIG. 2. FIG. 8 is a cross sectional schematic view which shows the flow of the body fluid in the width direction W of the absorbent article 1, and corresponds to the VII-VII cross section of FIG. 2. FIG. 9 is a cross sectional view at the IX-IX cross section of FIG. 2.

The absorbent article 1 includes the longitudinal direction L that includes the front side FD and the rear side RD, the width direction W, and the thickness direction T, and further includes the longitudinal direction axis line LA and the width direction axis line WA.

Further, the absorbent article 1 is partitioned into the front body FP and the rear body RP, and includes the front waist region FW, the rear waist region RW, and the crotch region C (the front crotch region FC and the rear crotch region RC).

Incidentally, the absorbent article 1 includes, as shown in FIG. 1, the pair of leakage prevention walls 101 that include the elastic members 103, the fixing portions 105 so as to fix the leakage prevention walls 101 to the liquid permeable sheet 3, the elastic members 107, and tape fasteners 109, etc., however, since these are known in the technical field, the explanation thereof is omitted.

The absorbent article 1 includes the liquid permeable sheet 3, the liquid impermeable sheet 5, and the absorbent body 7 which is placed between the liquid permeable sheet 3 and the liquid impermeable sheet 5.

The absorbent body 7 includes the longitudinal direction L, the width direction W, and the thickness direction T, which are the same as those of the absorbent article 1, and is configured by the absorbent core 9 which includes the skin facing surface 11 and the skin non-facing surface 13, and the core wrap 15 which is formed by tissue that covers the skin facing surface 11 and the skin non-facing surface 13 of the absorbent core 9.

The absorbent core 9 is configured by the first layer 17 which is arranged on the skin non-facing surface 13 (the liquid impermeable sheet 5) side, and the second layer 19 which is arranged on the skin facing surface 11 (the liquid permeable sheet 3) side. The first layer 17 and the second layer 19 are mutually adjacent to each other in the thickness direction T. Each of the first layer 17 and the second layer 19 includes the pulp fibers 21 and the superabsorbent polymers 23.

The first layer 17 includes the groove portion 25 and the base portion 29 which are arranged in the front body FP. The groove portion 25 extends along the longitudinal direction L, penetrates the first layer 17 in the thickness direction T, and includes the terminal edge 27 at the position which is the closest to the rear side RD of the groove portion 25. The base portion 29 is arranged at the position closer to the rear side RD of the groove portion 25 with the terminal edge 27 sandwiched in between. The base portion 29 is adjacent to the groove portion 25 with the terminal edge 27 sandwiched in between.

Incidentally, the groove portion 25 is configured by the groove portion 25$n$ (wherein n is a, b, c, d, e, or f), the terminal edge 27 is configured by the terminal edge 27$n$ (wherein n is a, b, c, d, e, or f), and the base portion 29 is configured by the base portion 29$n$ (wherein n is a, b, c, d, e, or f). The groove portion 25$n$ includes the terminal edge 27$n$, and each base portion 29$n$ is arranged at the position on the rear side RD of the groove portion 25$n$ with the terminal edge 27$n$ sandwiched in between (wherein n is a, b, c, d, e, or f).

Incidentally, in the present description, in order to simplify the explanation, the groove portion 25$a$, the terminal edge 27$a$, and the base portion 29$a$ are explained as the representatives of the groove portion 25, the terminal edge 27, and the base portion 29, respectively, however, the relationships between the other groove portion 25$n$, the terminal edge 27$n$, and the base portion 29$n$ (wherein n is b, c, d, e, or f) are the same.

Incidentally, the absorbent core 9 includes the groove portion 31 (the groove portion 31$a$, the groove portion 31$b$, the groove portion 31$c$, and the groove portion 31$d$) which does not include the terminal edge at the position which is the closest to the rear side RD, however, the explanation thereof is omitted.

As shown in FIG. 5, the second layer 19 includes, at the position which overlaps with the groove portion 25a and the base portion 29a in the thickness direction T, the groove portion corresponding portion 33a and the base portion corresponding portion 35a, respectively.

Incidentally, the second layer 19 includes, at the position which overlaps with the groove portion 25 and the base portion 29 in the thickness direction T, the groove portion corresponding portion 33 and the base portion corresponding portion 35, respectively. The groove portion corresponding portion 33 is configured by the groove portion corresponding portion 33n (wherein n is a, b, c, d, e, or f), and the base portion corresponding portion 35 is configured by the base portion corresponding portion 35n (wherein n is a, b, c, d, e, or f), however, only the portion thereof are shown in the drawings.

Incidentally, in the present description, in order to simplify the explanation, the groove portion corresponding portion 33a and the base portion corresponding portion 35a are explained as the representatives of the groove portion corresponding portion 33n (wherein n is a, b, c, d, e, or f) and the base portion corresponding portion 35n (wherein n is a, b, c, d, e, or f), respectively, however, the relationships between the other the groove portion corresponding portion 33n (wherein n is b, c, d, e, or f) and the base portion corresponding portion 35n (wherein n is b, c, d, e, or f) are the same.

As shown in FIG. 5, each of the average density of the superabsorbent polymers 23 included in the base portion 29a and the average density of the superabsorbent polymers 23 included in the base portion corresponding portion 35a is larger than the average density of the superabsorbent polymers 23 included in the groove portion corresponding portion 33a. Further, the average density of the superabsorbent polymers 23 included in the base portion corresponding portion 35a is larger than the average density of the superabsorbent polymers 23 included in the base portion 29a.

Referring to FIG. 6 and other drawings if necessary, when the body fluid of the wearer, such as urine, is supplied in spots in the vicinity of the boundary of the front waist region FW and the front crotch region FC (which corresponds to the excretory opening contact region) of the absorbent article 1, the body fluid moves to the rear side RD on the surface of the absorbent article 1 with the surface flow velocity V.

The groove portion corresponding portion 33a in which the average density of the superabsorbent polymers 23 is relatively smaller draws the body fluid which flows on the surface of the absorbent article 1, and subsequently makes the body fluid move to the groove portion 25a in which the material density is approximately 0. The groove portion 25a makes the body fluid move to the rear side RD with the first layer groove portion flow velocity $V1_A$ until the groove portion 25a itself is filled with the body fluid. Although material density of the groove portion 25a is approximately 0, since the materials which configure the absorbent core 9 and the core wrap 15 are present in the surroundings, the first layer groove portion flow velocity $V1_A$ is to be slower than the surface flow velocity V.

On the other hand, since the groove portion corresponding portion 33a has the larger material density than the groove portion 25a, the groove portion corresponding portion 33a makes the body fluid move to the rear side RD with the second layer groove portion corresponding portion flow velocity $V2_A$ which is slower than the first layer groove portion flow velocity $V1_A$.

In the surface flow velocity V, the first layer groove portion flow velocity $V1_A$, and the second layer groove portion corresponding portion flow velocity $V2_A$, the following relationship formula 1a is established.

the surface flow velocity V>the first layer groove portion flow velocity $V1_A$>the second layer groove portion corresponding portion flow velocity $V2_A$ Further, in the rear side RD of the groove portion 25a of the first layer 17, since the base portion 29a in which the average density of the superabsorbent polymers 23 is relatively larger than that of the groove portion 25a is present, the base portion 29a once blocks the body fluid which is present in the groove portion 25a, and while the superabsorbent polymers 23 which are present in the base portion 29a absorb the body fluid which is present in the groove portion 25a, the superabsorbent polymers 23 make the body fluid which is present in the groove portion 25a permeate (move) to the rear side RD with the first layer base portion flow velocity $V1_B$ which is slower than the surface flow velocity V.

Further, in the rear side RD of the groove portion corresponding portion 33a of the second layer 19, since the base portion corresponding portion 35a in which the average density of the superabsorbent polymers 23 is relatively larger than that of the groove portion corresponding portion 33a is present, the base portion corresponding portion 35a once blocks the body fluid which is present in the groove portion corresponding portion 33a, and while the superabsorbent polymers 23 which are present in the base portion corresponding portion 35a absorb the body fluid which is present in the groove portion corresponding portion 33a, the superabsorbent polymers 23 make the body fluid which is present in the groove portion corresponding portion 33a permeate (move) to the rear side RD with the second layer base portion corresponding portion flow velocity $V2_B$ which is slower than the surface flow velocity V.

Still further, since the average density of the superabsorbent polymers 23 included in the base portion corresponding portion 35a is larger than the average density of the superabsorbent polymers 23 included in the base portion 29a, there is a tendency that the second layer base portion corresponding portion flow velocity $V2_B$ is to be slower than the first layer base portion flow velocity $V1_B$.

In the surface flow velocity V, the first layer base portion flow velocity $V1_B$, and the second layer base portion corresponding portion flow velocity $V2_B$, the following relationship formula 2a is established.

the surface flow velocity V>the first layer base portion flow velocity $V1_B$>the second layer base portion corresponding portion flow velocity $V2_B$ As described above, in the surface flow velocity V, the first layer average flow velocity V1, and the second layer average flow velocity V2, the following relationship formula 3a is established, the surface flow velocity V>the first layer average flow velocity V1>the second layer average flow velocity V2 and the body fluid can be made to move to the rear side RD of the absorbent core step 9 step by step, whereby it is easy for the absorbent article 1 to make the body fluid flow in the longitudinal direction L of the absorbent core 9 and it is difficult for the leakage to occur in the crotch region C (especially in the rear crotch region RC which is often at the lowest position when being worn).

Further, the groove portion 25a and the groove portion 25b extend in the direction which intersects with the longitudinal direction L at the position on the front side FD with respect to the terminal edge 27a and the terminal edge 27b, respectively. To be specific, each of the groove portion 25a and the groove portion 25b is arranged toward the rear side RD so as to approach the longitudinal direction axis line LA of the absorbent core 9 and to have an intersecting angle θ with the longitudinal direction axis line. Accordingly, the routes of the groove portion 25a and the groove portion 25b of the first layer 17 and the routes of the groove portion corresponding portion 33 of the second layer 19 corresponding thereto can be made to be longer, whereby the time which takes for the body fluid that moves inside the first layer 17 and the second layer 19 to the rear side RD to reach the crotch region C (especially the rear crotch region RC) can be made to be slower, so that it is difficult for the leakage to occur in the crotch region C (especially in the rear crotch region RC).

Still further, each of the groove portion 25a and the groove portion 25b is arranged toward the rear side RD so as to approach the longitudinal direction axis line LA of the absorbent core 9, whereby when the body fluid flows to the rear side RD along the groove portion 25a and the groove portion 25b, the body fluid flows toward the center in the width direction W of the absorbent article 1 (the absorbent core 9), and thus it is difficult for the leakage to occur in the crotch region C (especially in the rear crotch region RC).

As shown in FIG. 7, in the absorbent article 1 according to the first embodiment, the first layer 17 further includes the pair of width direction base portions 41 (specifically, the width direction base portions 41a) which are arranged adjacent to the both side in the width direction W of the groove portion 25 (specifically, the groove portion 25a). Further, the second layer 19 further includes the pair of width direction base portion corresponding portions 43 (specifically, the width direction base portion corresponding portions 43a) which are arranged at the positions that overlap with the pair of width direction base portions 41 (specifically, the pair of width direction base portions 41a) in the thickness direction T.

Each of the average density of the superabsorbent polymers 23 included in each of the pair of width direction base portions 41 (specifically, the pair of width direction base portions 41a) and the average density of the superabsorbent polymers 23 included in the groove portion corresponding portion 33 (specifically, the groove portion corresponding portion 33a) is smaller than the average density of the superabsorbent polymers 23 included in each of the pair of width direction base portion corresponding portions 43 (specifically, the pair of width direction base portion corresponding portions 43a). Further, the average density of the superabsorbent polymers 23 included in the groove portion corresponding portion 33 (specifically, the groove portion corresponding portion 33a) is smaller than the average density of the superabsorbent polymers 23 included in each of the pair of width direction base portions 41 (specifically, the pair of width direction base portions 41a).

Accordingly, the body fluid which is blocked by the base portion 29a and is present in the base portion 29a is absorbed by the width direction base portions 41a which includes the superabsorbent polymers 23 as shown in the arrow A of FIG. 8 (the arrow A). Subsequently, the body fluid which can no longer be retained by the width direction base portions 41a is absorbed and retained by the width direction base portion corresponding portions 43a which has a larger average density of the superabsorbent polymers 23 than the width direction base portions 41a as shown in the arrow B of FIG. 8.

Further, each of the groove portion corresponding portion 33a, the width direction base portions 41a, and the width direction base portion corresponding portions 43a includes the predetermined amount of the superabsorbent polymers 23, whereby the swelling of the width direction base portions 41a and the groove portion corresponding portion 33a which are present in the surrounding of the groove portion 25a is suppressed, and it is easier for the length w in the width direction W and the height h in the thickness direction T of the groove portion 25a to be maintained, and thus it is easier for the water flow function of the groove portion 25a to be secured. Accordingly, according to the absorbent article 1, it is easy to make the body fluid flow in the longitudinal direction L of the absorbent core 9 and it is difficult for the leakage to occur in the crotch region C (especially in the rear crotch region RC).

Incidentally, the first layer 17 further includes, other than the groove portion 25a, the pair of width direction base portions (which are not shown) that correspond to each of the groove portions 25n (wherein n is b, c, d, e, or f), and the second layer 19 further includes, other than the groove portion 25a, the pair of width direction base portion corresponding portions (which are not shown) that correspond to each of the groove portions 25n (wherein n is b, c, d, e, or f), however, since these relationships are the same as those of the groove portion 25a, the pair of width direction base portions 41a, and the pair of width direction base portion corresponding portions 43a, the drawing and the explanation there of are omitted.

The groove portion 25 further includes the subordinate groove portion 51 which penetrates the first layer 17 in the thickness direction T and extends in the direction which intersects with the groove portion 25 (specifically, the width direction W). The subordinate groove portion 51 includes the subordinate groove portion base edge 53 and the subordinate groove portion terminal edge 55, and the subordinate groove portion base edge 53 is connected to the groove portion 25.

Further, the second layer 19 further includes the subordinate groove portion corresponding portion 57 at the position which overlaps with the subordinate groove portion 51 in the thickness direction T.

Incidentally, the subordinate groove portion 51 is configured by the subordinate groove portion 51n which corresponds to the groove portion 25n, the subordinate groove portion base edge 53 is configured by the subordinate groove portion base edge 53n which corresponds to the groove portion 25n, the subordinate groove portion terminal edge 55 is configured by the subordinate groove portion terminal edge 55n which corresponds to the groove portion 25n, and the subordinate groove portion corresponding portion 57 is configured by the subordinate groove portion corresponding portion 57n which corresponds to the groove portion 25n (wherein n is a, b, c, d, e, or f, however, only a portion thereof is shown in the drawings), however, a case in which n is a is explained as a representative.

Incidentally, the case in which n is b, c, d, e, or f is the same as the case in which n is a, and thus although shown in the drawings (except for the subordinate groove portion corresponding portion 57n), the explanation thereof is omitted.

As shown in FIG. 9, the average density of the superabsorbent polymers 23 included in the subordinate groove portion corresponding portion 57a is smaller than the average density of the superabsorbent polymers 23 included in each of the pair of width direction base portion corresponding portions 43a. Accordingly, it is easier for the subordinate groove portion corresponding portion 57a to have the same effect as the groove portion corresponding portion 33a. To be specific, it is easier for the subordinate groove portion corresponding portion 57a of the second layer 19 to make the body fluid permeate in the thickness direction T, and to make the body fluid move to the subordinate groove portion 51a.

Further, as shown in FIG. 9, the average density of the superabsorbent polymers 23 included in the subordinate groove portion corresponding portion 57a is smaller than the average density of the superabsorbent polymers 23 included in each of the pair of width direction base portions 41a. Accordingly, it is easier for the subordinate groove portion corresponding portion 57a to have same effect as the groove portion corresponding portion 33a.

Still further, the subordinate groove portion 51a includes the subordinate groove portion terminal edge 55a, and the absorbent core 9 includes, at the tip of the subordinate groove portion terminal edge 55a of the subordinate groove portion 51a, the pulp fibers 21 and the superabsorbent polymers 23 which configure the absorbent core 9.

Accordingly, it is easier for the body fluid which has reached the subordinate groove portion terminal edge 55a of the subordinate groove portion 51a to permeate inside the width direction base portions 41a (and the base portion 29a) through the subordinate groove portion terminal edge 55a, and for the body fluid to be absorbed by the absorbent core 9, for example, the pair of width direction base portion corresponding portions 43a.

Further, by the presence of the subordinate groove portion 51, it is easier to induce the deformation of the absorbent core 9, and the absorbent article 1, in the longitudinal direction L, and while the absorbent article 1 fits the body of the wearer, it is easier to prevent the liquid leakage.

Figure 10:
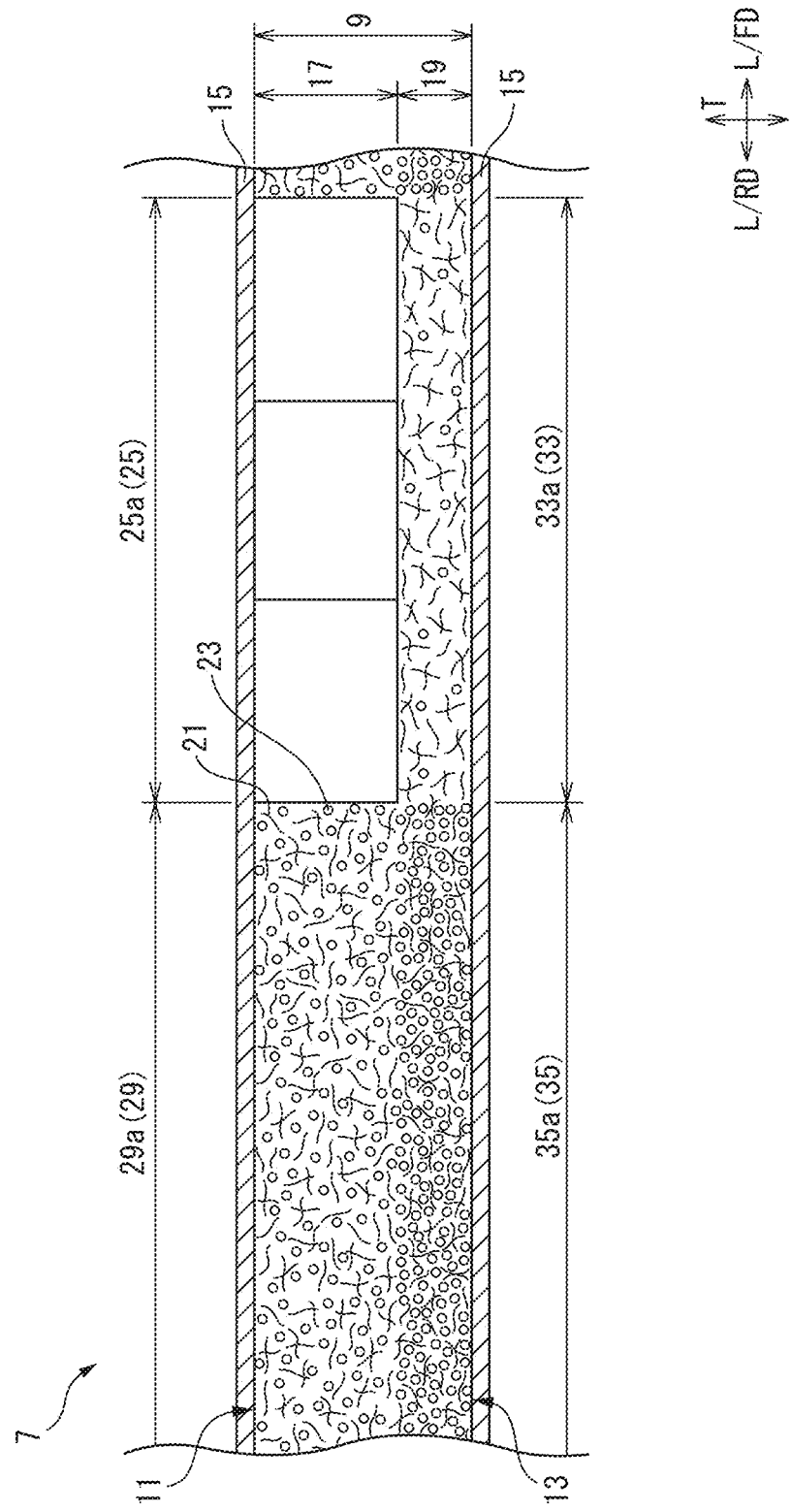
FIG. 10 is a diagram so as to explain the absorbent article according to the second embodiment.
Figure 11:
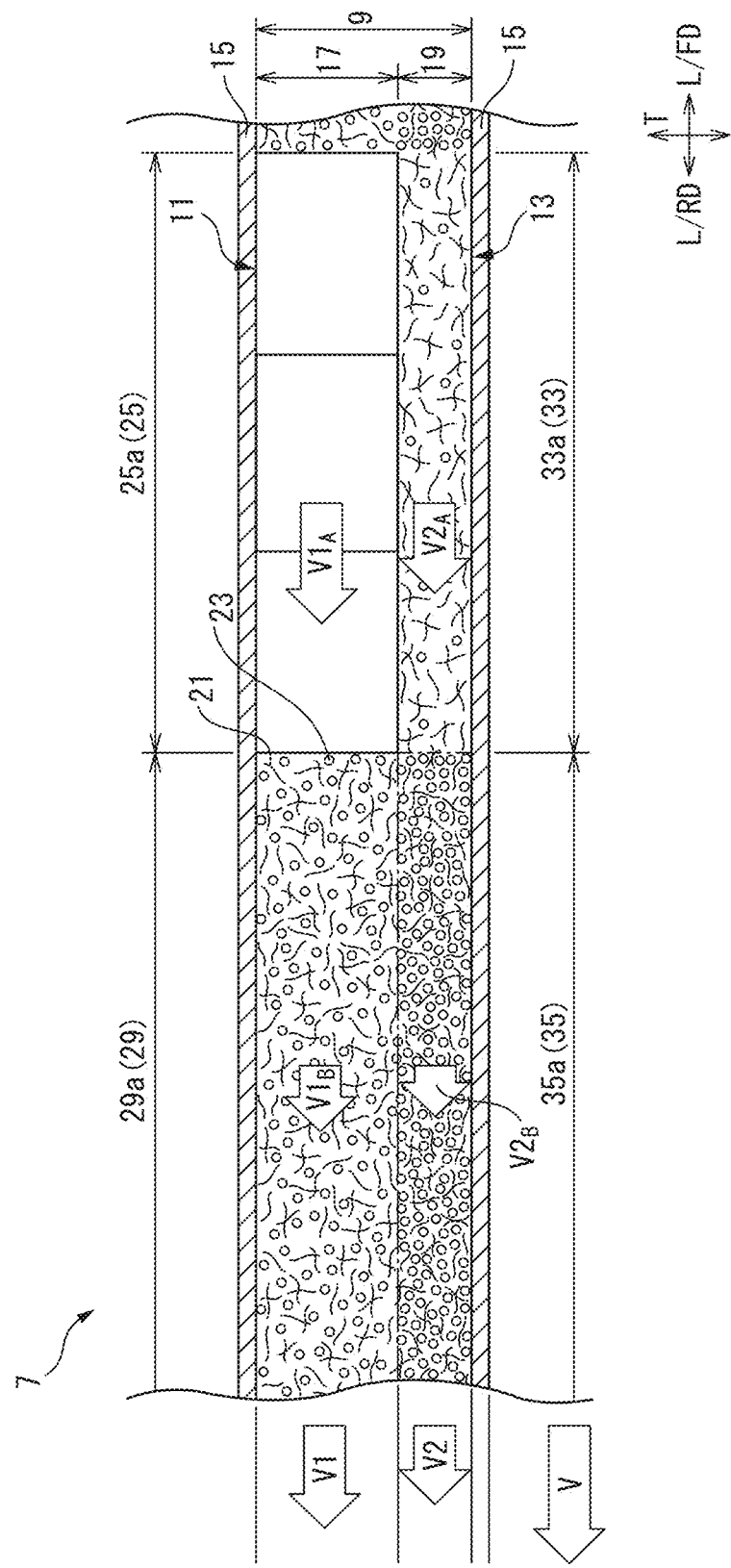
FIG. 11 is a diagram so as to explain the absorbent article according to the second embodiment.

FIG. 10 and FIG. 11 are diagrams so as to explain the absorbent article according to another embodiment of the present disclosure (hereinbelow, which may be referred to as "the second embodiment"), and correspond to the cross sectional diagram at the V-V cross section of FIG. 2.

As shown in FIG. 10, the absorbent article according to the second embodiment is the same as the absorbent article 1 according to the first embodiment except for the first layer 17 being arranged on the skin facing surface 11 (the liquid impermeable sheet) side and the second layer 19 being arranged on the skin non-facing surface 13 (the liquid permeable sheet) side in the absorbent core 9 which configures the absorbent body 7, and accordingly, the absorbent article according to the second embodiment is explained with reference to FIG. 1 to FIG. 9 as appropriate.

In the absorbent article according to the second embodiment, when the body fluid of the wearer, such as urine, is supplied in spots in the boundary region of the front waist region FW and the front crotch region FC (which corresponds to the excretory opening contact region) of the absorbent article 1, the body fluid moves to the rear side RD on the surface of the absorbent article 1 with the surface flow velocity V.

The groove portion 25a of the first layer 17 in which the material density is approximately 0 draws the body fluid which flows on the surface of the absorbent article 1. The groove portion 25a makes the body fluid move to the rear side RD with the first layer groove portion flow velocity $V1_A$ until the groove portion 25a itself is filled with the body fluid.

Although material density of the groove portion 25a is approximately 0, since the materials which configure the absorbent core 9 and the core wrap 15 are present in the surroundings, the first layer groove portion flow velocity $V1_A$ is to be slower than the surface flow velocity V.

The groove portion corresponding portion 33a draws the body fluid from the groove portion 25a by the capillary phenomenon, etc., and makes the body fluid move to the rear side RD with the second layer groove portion corresponding portion flow velocity $V2_A$. Since the material density of the groove portion corresponding portion 33a is larger than that of the groove portion 25a, the second layer groove portion corresponding portion flow velocity $V2_A$ is to be slower than the first layer groove portion flow velocity $V1_A$.

In the surface flow velocity V, the first layer groove portion flow velocity $V1_A$, and the second layer groove portion corresponding portion flow velocity $V2_A$, the following relationship formula 1a is established.

the surface flow velocity V>the first layer groove portion flow velocity $V1_A$>the second layer groove portion corresponding portion flow velocity $V2_A$ In the rear side RD of the groove portion corresponding portion 33a of the second layer 19, since the base portion corresponding portion 35a in which the average density of the superabsorbent polymers 23 is relatively larger than that of the groove portion corresponding portion 33a is present, the base portion corresponding portion 35a once blocks the body fluid which is present in the groove portion corresponding portion 33a, and while the superabsorbent polymers 23 which are present in the base portion corresponding portion 35a absorb the body fluid which is present in the groove portion corresponding portion 33a, the superabsorbent polymers 23 make the body fluid which is present in the groove portion corresponding portion 33a permeate to the rear side RD with the second layer base portion corresponding portion flow velocity $V2_B$ which is slower than the surface flow velocity V.

Further, in the rear side RD of the groove portion 25a of the first layer 17, since the base portion 29a in which the average density of the superabsorbent polymers 23 is relatively larger than that of the groove portion 25a is present, the base portion 29a once blocks the body fluid which is present in the groove portion 25a, and while the superabsorbent polymers 23 which are present in the base portion 29a absorb the body fluid which is present in the groove portion 25a, the superabsorbent polymers 23 can make the body fluid which is present in the groove portion 25a permeate to the rear side RD with the first layer base portion flow velocity $V1_B$ which is slower than the surface flow velocity V.

Incidentally since the average density of the superabsorbent polymers 23 included in the base portion corresponding portion 35a is larger than the average density of the superabsorbent polymers 23 included in the base portion 29a, there is a tendency that the second layer base portion corresponding portion flow velocity $V2_B$ is to be slower than the first layer base portion flow velocity $V1_B$.

In the surface flow velocity V, the first layer base portion flow velocity $V1_B$, and the second layer base portion corresponding portion flow velocity $V2_B$, the following relationship formula 2a is established.

the surface flow velocity V>the first layer base portion flow velocity $V1_B$>the second layer base portion corresponding portion flow velocity $V2_B$ As described above, in the surface flow velocity V, the first layer average flow velocity V1, and the second layer average flow velocity V2, the following relationship formula 3a is established, the surface flow velocity V>the first layer average flow velocity V1>the second layer average flow velocity V2
and the body fluid can be made to move to the rear side RD of the absorbent core step 9 step by step, whereby it is easy for the absorbent article 1 to make the body fluid flow in the longitudinal direction L of the absorbent core 9 and it is difficult for the leakage to occur in the crotch region C (especially in the rear crotch region RC).

Figure 12:
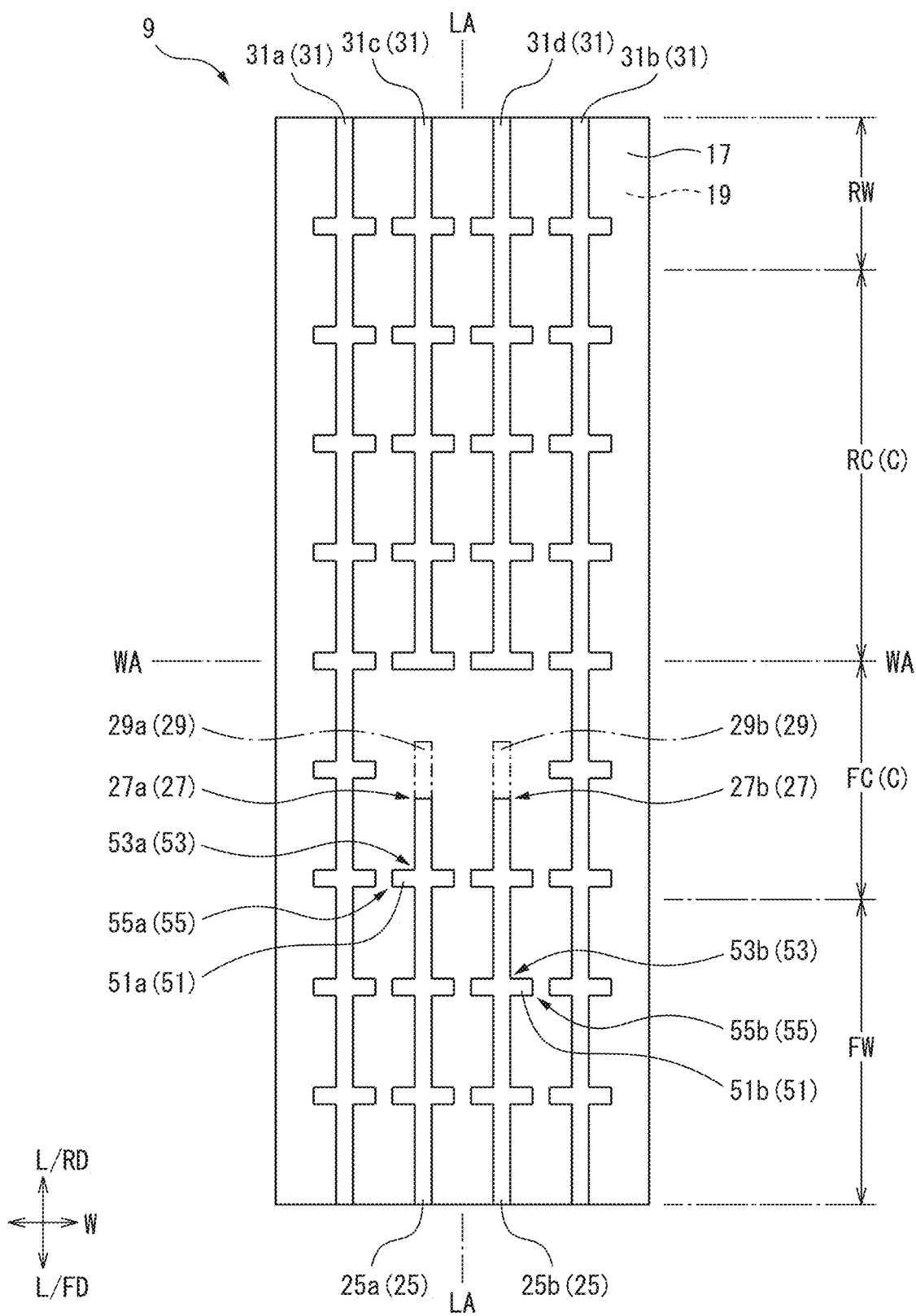
FIG. 12 is a diagram so as to explain the modification example of the absorbent core 9.

FIG. 12 is a diagram so as to explain the modification example of the absorbent core 9 in the absorbent article according to the present disclosure. The absorbent core 9 includes the longitudinal direction axis line LA, and the width direction axis line WA, and further includes the front waist region FW, the crotch region C (the front crotch region FC and the rear crotch region RC), and the rear waist region RW.

The absorbent core 9 includes the first layer 17 and the second layer 19 which are mutually adjacent to each other in the thickness direction T (which is not shown) of the absorbent core 9, and the first layer 17 includes (i) the groove portion 25 which extends along the longitudinal direction L, penetrates in the thickness direction (which is not shown), and includes the terminal edge 27 at the position which is the closest to the rear side RD, and (ii) the base portion 29 which is arranged at the position closer to the rear side RD of the groove portion 25 with the terminal edge 27 sandwiched in between, which are arranged in the front body FP. The groove portion 25 is present so as to be connected to the groove portion 25 through the subordinate groove portion base edge 53 in the direction which intersects with the groove portion 25 (the width direction W), and further includes the plurality of subordinate groove portions 51 each of which having the subordinate groove portion terminal edge 55 on the opposite side of the subordinate groove portion base edge 53.

The groove portion 25 is configured by the groove portion 25a and the groove portion 25b, the terminal edge 27 is configured by the terminal edge 27a and the terminal edge 27b, and the base portion 29 is configured by the base portion 29a and the base portion 29b.

The first layer 17 further includes the groove portion 31 (the groove portion 31a, the groove portion 31b, the groove portion 31c, and the groove portion 31d) which does not include the terminal edge at the position closest to the rear side RD.

The groove portion 25a further includes the subordinate groove portion 51a which includes the subordinate groove portion base edge 53a and the subordinate groove portion terminal edge 55a, and is connected to the groove portion 25a through the subordinate groove portion base edge 53a. The groove portion 25b further includes the subordinate groove portion 51b which includes the subordinate groove portion base edge 53b and the subordinate groove portion terminal edge 55b, and is connected to the groove portion 25b through the subordinate groove portion base edge 53b.

Figure 13:
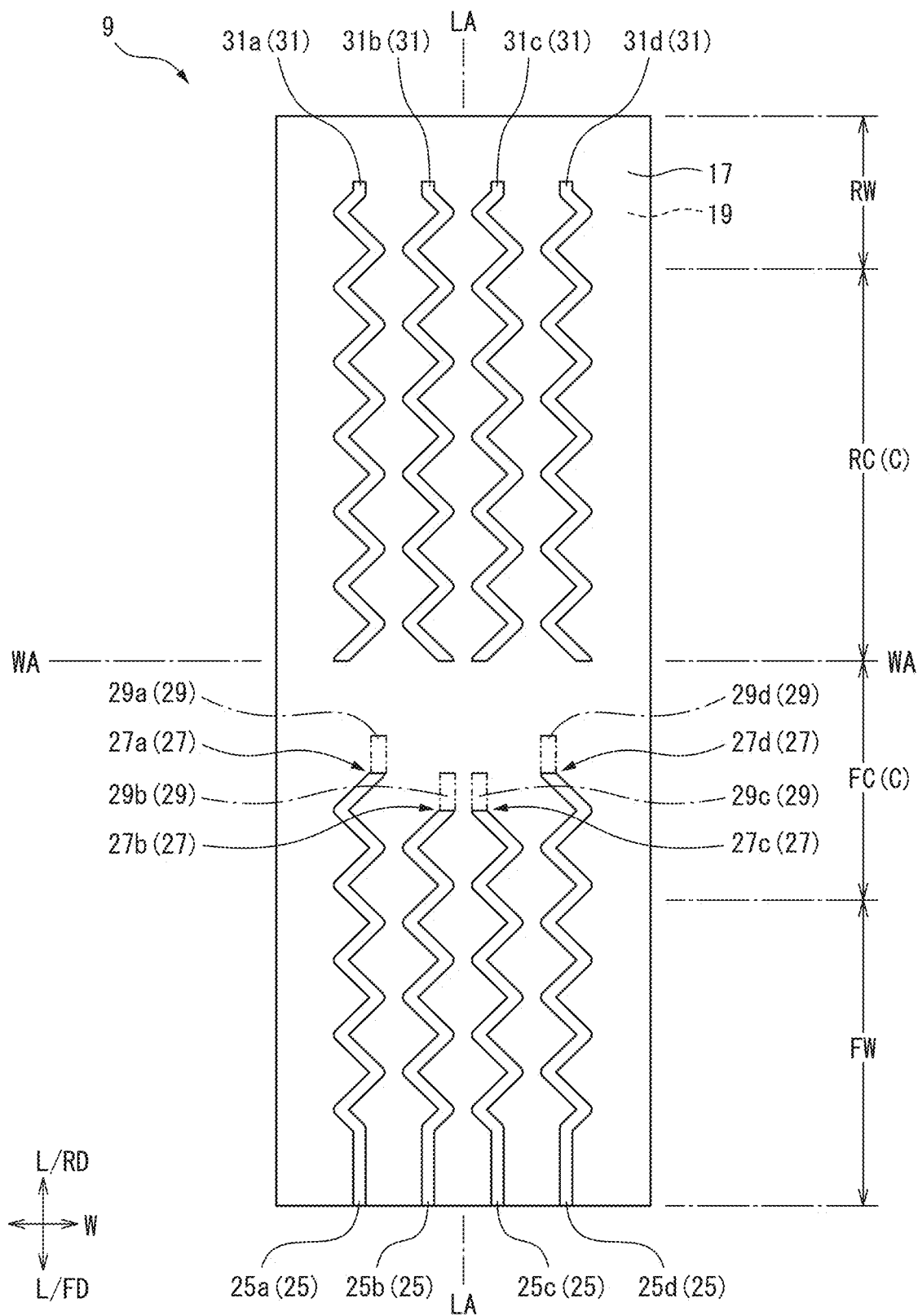
FIG. 13 is a diagram so as to explain another modification example of the absorbent core 9.

FIG. 13 is a diagram so as to explain another modification example of the absorbent core 9 in the absorbent article according to the present disclosure. The absorbent core 9 includes the longitudinal direction axis line LA, and the width direction axis line WA, and further includes the front waist region FW, the crotch region C (the front crotch region FC and the rear crotch region RC), and the rear waist region RW.

The absorbent core 9 includes the first layer 17 and the second layer 19 which are mutually adjacent to each other in the thickness direction T (which is not shown) of the absorbent core 9, and the first layer 17 includes (i) the groove portion 25 which extends along the longitudinal direction L, penetrates in the thickness direction (which is not shown), and includes the terminal edge 27 at the position which is the closest to the rear side RD, and (ii) the base portion 29 which is arranged at the position closer to the rear side RD of the groove portion 25 with the terminal edge 27 sandwiched in between, which are arranged in the front body FP.

The groove portion 25 is configured by the groove portion 25a, the groove portion 25b, the groove portion 25c, the groove portion 25d, the terminal edge 27 is configured by the terminal edge 27a, the terminal edge 27b, the terminal edge 27c, and the terminal edge 27d, and the base portion 29 is configured by the base portion 29a, the base portion 29b, the base portion 29c, and the base portion 29d.

The first layer 17 further includes the groove portion 31 (the groove portion 31a, the groove portion 31b, the groove portion 31c, and the groove portion 31d) which is arranged in the rear body RP.

In the absorbent article according to the present disclosure, the first layer and second layer may be arranged on the skin contact surface side and the skin non-contact surface side, or the skin non-contact surface side and the skin contact surface side, respectively, as long as the first layer and second layer are mutually adjacent to each other in the thickness direction of the absorbent article.

Further, the absorbent core may include an additional layer, such as the third layer which is arranged on the skin contact surface side (for example, a layer which includes pulp fibers, or a layer which is consisted of pulp fibers), and the third layer which is arranged on the skin non-contact surface side (for example, a layer which includes superabsorbent polymers, or a layer which is consisted of superabsorbent polymers), other than the first layer and the second layer.

As the superabsorbent polymers which are included in the absorbent core according to the present disclosure, those which are known in the technical field may be adopted without particular limitation, and as such superabsorbent polymers, for example, particles of superabsorbent polymers of polyacrylate-based, polysulfonate-based, maleic anhydride-based, polyacrylamide-based, polyvinyl alcohol-based, polyethylene oxide-based, polyaspartate-based, polyglutamate-based, polyalginate-based, starch-based, and cellulose-based, etc.; superabsorbent polymers of starch-based, or cellulose-based such as starch-acrylic acid (salt) graft copolymer, saponified starch-acrylonitrile copolymer, cross-linked sodium carboxymethyl cellulose, etc., may be mentioned.

In the absorbent core according to the present disclosure, the first layer includes the superabsorbent polymers with the average basis weight of preferably 30 to 100 $g/m^2$, and more preferably 40 to 60 $g/m^2$, and the second layer includes the superabsorbent polymers with the average basis weight of preferably 100 to 180 $g/m^2$, and more preferably 120 to 160 $g/m^2$. Further, the first layer and the second layer include the superabsorbent polymers, with the basis of the total mass of the superabsorbent polymers included in the first layer and the second layer, preferably 20 to 45 mass % and 55 to 80 mass %, and more preferably 25 to 35 mass % and 65 to 75 mass %.

The absorbent article according to the present disclosure may include, in addition to the superabsorbent polymers, other materials known in the technical field, such as fibers, such as natural fibers, synthetic fibers, and semi-synthetic fibers. As the natural fibers, pulp fibers and regenerated cellulose fibers may be mentioned. As the regenerated cellulose fibers, rayon fibers, such as viscose rayon which is obtained from viscose, polynosic, modal, copper ammonia rayon fibers which are obtained from a solution of cellulose in a copper ammonia salt (which is also referred to as "cupra"); lyocell and tencel obtained by an organic solvent spinning method using an organic solvent that is a mixed solution of an organic compound and water, and without a cellulose derivative, etc., may be mentioned.

As the semi-synthetic fibers, semi-synthetic cellulose fibers, such as acetate fibers, such as triacetate fibers and diacetate fibers may be mentioned.

In the absorbent article according to the present disclosure, in a case in which the absorbent core includes fibers, each of the first layer and the second layer includes the fibers with the basis weight of preferably 50 to 150 $g/m^2$, and more preferably 80 to 100 $g/m^2$.

The absorbent article according to the present disclosure may further include a core wrap which covers the skin contact surface and/or the skin non-contact surface of the absorbent core. Especially, when the absorbent core is arranged so as to come into contact with the first layer of the absorbent core, it is difficult for the groove portion of the first layer to be crushed.

Further, in the above-mentioned case, it is preferable that the core wrap is arranged so as to protrude toward the second layer in the groove portion. This is from the viewpoint of the effect which is described in the aspect 12.

Incidentally, the absorbent core and the core wrap which covers the absorbent core may altogether be referred to as the absorbent body. As the core wrap, those which are known in the technical field, for example, tissue, nonwoven fabric (such as an air-through nonwoven fabric) may be mentioned.

In the absorbent article according to the present disclosure, the thickness of each of the first layer and the second layer is preferably 0.1 to 5.0 mm, more preferably 0.5 to 4.0 mm, and even more preferably 1.0 to 3.0 mm The thickness of each of the first layer and the second layer may be measured in the following non-contact method by using the laser displacement meter (for example, High-precision two-dimensional laser displacement meter LJ-G series (model: LJ-G030) manufactured by Keyence Corporation).

The absorbent core which is obtained by blowing a cold spray onto an absorbent article so as to peel off the liquid permeable sheet, the liquid impermeable sheet, and the core wrap, is cut out into the size of 100 mm×100 mm, and is regarded as a sample. The sample is placed on a horizontal measurement table so that the first layer which includes the groove portion and the base portion faces upward, the displacement from the measurement table is measured by the laser displacement meter for five different base portions, and the average value of the five measurement values is set as Ax (mm). In the same manner, the displacement from the measurement table is measured by the laser displacement meter for five different groove portions, and the average value of the five measurement values is set as Ay (mm). The thickness of the second layer is the above-mentioned Ay (mm), and the thickness of the first layer is calculated from the difference of the above-mentioned Ax (mm) and above-mentioned Ay (mm).

In the absorbent article according to the present disclosure, the first layer of the absorbent core includes the groove portion which is arranged in the front body and extends along the longitudinal direction of the absorbent article, penetrates in the thickness direction of the absorbent article, and includes the terminal edge at the position on the rear side (hereinbelow, which may be referred to as "the specified groove portion"), and may further include the non-specified groove portion, such as the groove portion which is arranged in the rear body, for example, the groove portion which is arranged only in the rear body, or the groove portion which is arranged across the front body to the rear body.

In the absorbent article according to the present disclosure, the specified groove portion which the first layer includes is arranged in the front body in a plan view. In a case in which the absorbent article according to the present disclosure is for a female, it is preferable that the specified groove portion is arranged at least in the front crotch region, and in a case in which the absorbent article according to the present disclosure is for a male, it is preferable that the specified groove portion is arranged at least in the front waist region, and preferably at both of the front waist region and the front crotch region. Further, in a case in which the absorbent article according to the present disclosure is for both of a male and a female, it is preferable that the specified groove portion is arranged at both of the front waist region and the front crotch region.

This is because it is preferable that the specified groove portion is arranged in the excretory opening contact region, and on the rear side of the excretory opening contact region.

Incidentally, the terminal edge which the specified groove portion includes means the edge which is arranged at the position on the most rear side in the groove portion.

In the absorbent article according to the present disclosure, the first layer preferably includes 1 or more, more preferably 2 or more, even more preferably 3 or more, and still more preferably 4 or more of the above-mentioned specified groove portions. This is from the viewpoint of the effect of the present disclosure. Further, in the absorbent article according to the present disclosure, the first layer preferably includes 15 or less, more preferably 10 or less, even more preferably 8 or less, and still more preferably 6 or less of the above-mentioned specified groove portions. This is because, when there are too many specified groove portions, the action of a single specified groove portion is to be reduced.

In the absorbent article according to the present disclosure, the specified groove portion which the first layer includes has a width of preferably 0.5 to 3.0 times, more preferably 0.8 to 2.5 times, and even more preferably 1.0 to 2.0 times as much of the thickness of the absorbent core (or the absorbent body). When the width of the specified groove portion is within the above-mentioned range, it is difficult for the specified groove portion to be crushed even after the absorbent article absorbs the body fluid.

In the present description, the thickness (mm) of the absorbent core (or the absorbent body) is measured in the following manner FS-60DS [the measurement surface: 44 mm (in diameter), the measurement pressure: 3 $g/cm^2$] manufactured by Daiei Kagaku Seiki MFG, Co., Ltd. is prepared, five different portions of the absorbent core (or the absorbent body) are applied with pressure under the standard condition (the temperature: 23±2° C., the relative humidity: 50±5%), the thickness at each of the portions 10 seconds after being applied with pressure is measured, and the average value of the 5 measurement values is regarded as the thickness of the absorbent core (or the absorbent body).

In the absorbent article according to the present disclosure, the first layer of the absorbent core includes the base portion which is arranged adjacent to the position on the rear side of the groove portion with the above-mentioned edge sandwiched in between. The base portion extends to the rear side in the longitudinal direction parallel to the longitudinal axis line from the terminal edge of the specified groove portion.

The base portion has the length in the longitudinal direction preferably 0.5 to 10.0 times, more preferably 0.7 to 7.0 times, and even more preferably 1.0 to 5.0 times as much of the width of the groove portion with the terminal edge taken as the starting point. This is from the viewpoint of the effect of the base portion.

In the absorbent article according to the present disclosure, since the groove portion corresponding portion and the base portion corresponding portion of the second layer are the portions which overlap in the thickness direction with the groove portion and the base portion of the first layer, respectively, the explanations thereof are omitted.

In the absorbent article according to the present disclosure, each of the average density of the superabsorbent polymers included in the base portion and the average density of the superabsorbent polymers included in the base portion corresponding portion is larger than the average density of the superabsorbent polymers included in the groove portion corresponding portion, and is larger by preferably 0.01 to 0.20 $g/cm^3$, and more preferably 0.05 to 0.20 $g/cm^3$. Further, the average density of the superabsorbent polymers included in the base portion corresponding portion is larger than the average density of the superabsorbent polymers included in the base portion, and is larger by preferably 0.01 to 0.15 $g/cm^3$, and more preferably 0.05 to 0.15 $g/cm^3$. This is from the viewpoint of the effect of the present disclosure.

Incidentally, in the absorbent article according to the present disclosure, the average density of the superabsorbent polymers included in the groove portion corresponding portion is preferably larger than 0 $g/cm^3$ and 0.15 $g/cm^3$ or smaller, and more preferably larger than 0 $g/cm^3$ and 0.10 $g/cm^3$ or smaller, the average density of the superabsorbent polymers included in the base portion is preferably larger than 0 $g/cm^3$ and 0.35 $g/cm^3$ or smaller, and more preferably larger than 0 $g/cm^3$ and 0.30 $g/cm^3$ or smaller, and the average density of the superabsorbent polymers included in the base portion corresponding portion is preferably larger than 0.10 $g/cm^3$ and 0.50 $g/cm^3$ or smaller, and more preferably larger than 0.10 $g/cm^3$ and 0.45 $g/cm^3$ or smaller.

In the present description, the average density of the superabsorbent polymers is measured in the following manner (1) Five or more samples of each of the portions of the base portion, the groove portion corresponding portion, and the base portion corresponding portion, etc., are cut out from the absorbent core so that each of the samples have a predetermined area (for example, 4 mm×4 mm) in a plan view.

(2) The thickness of each of the samples is measured by using the laser displacement meter (for example, High-precision two-dimensional laser displacement meter LJ-G series (model: LJ-G030) manufactured by Keyence Corporation).

(3) The superabsorbent polymers included in each of the samples are separated, the total mass of the superabsorbent polymers included in each of the samples is measured, the measurement value is divided by the later-described volume of the sample which is obtained by the thickness of the sample and the area of the sample, whereby the average density is obtained.

Further, in the present description, the degree of the average density of the superabsorbent polymers can be evaluated for example by the following manner An absorbent article is immersed in liquid nitrogen so as to be frozen, and then, the absorbent article is cut in the thickness direction, so as to obtain a sample of the cross section at the surface with intersects with the direction in which the groove portion extends. Subsequently, the sample is returned to room temperature and a cross sectional image with a magnification of 50 times is obtained by using an electron microscope (for example, VE7800 manufactured by Keyence Corporation). Further, in the cross sectional image, the degree (whether it is high or low) of the average density of the superabsorbent polymers at each of the portions of the base portion, the groove portion corresponding portion, and the base portion corresponding portion, etc., is visually evaluated.

Incidentally, the later-described average density of the superabsorbent polymers in the width direction base portion, the width direction base portion corresponding portion, and the subordinate groove portion corresponding portion can be measured or evaluated in the same manner as the above-mentioned methods.

In the absorbent article according to the present disclosure, it is preferable that the specified groove portion of the first layer extends in the direction which intersects with the longitudinal direction, and the axis line of the specified groove portion extends so as to have an intersecting angle of preferably 45° or less, and more preferably 30° or less, with respect to the longitudinal direction axis line at an arbitrary point. This is from the viewpoint of the effect of the present disclosure.

Further, the specified groove portion is preferably arranged toward the rear side so as to approach the longitudinal direction axis line. This is because the differences between each of the surface flow velocity, the first layer average flow velocity, and the second layer average flow velocity can be increased, and the body fluid can be made to move toward the rear side so as to approach the longitudinal axis line of the absorbent core, that is, the center in the width direction of the absorbent core.

In the absorbent article according to the present disclosure, it is preferable that the first layer further includes a pair of width direction base portions which are arranged adjacent to both sides in the width direction of the specified groove portion, and the second layer further includes a pair of width direction base portion corresponding portions which are arranged at positions which overlap with the pair of width direction base portions in the thickness direction, respectively. Further, it is preferable that each of the average density of the superabsorbent polymers included in each of the pair of width direction base portions and the average density of the superabsorbent polymers included in the groove portion corresponding portion is smaller than the average density of the superabsorbent polymers included in each of the pair of width direction base portion corresponding portions, and is smaller by more preferably 0.01 to 0.15 $g/cm^3$, and even more preferably 0.05 to 0.15 $g/cm^3$. This is from the viewpoint of the effect which is described in aspect 5.

Further, it is preferable that the average density of the superabsorbent polymers included in the groove portion corresponding portion is smaller than the average density of the superabsorbent polymers included in each of the pair of width direction base portions, and is smaller by more preferably 0.01 to 0.15 g/cm$^3$, and even more preferably 0.05 to 0.15 g/cm$^3$. This is from the viewpoint of the effect which is described in aspect 6.

In a case in which the absorbent article according to the present disclosure includes the above-mentioned pair of width direction base portions, each of the pair of width direction base portions has the width of preferably 0.5 to 5.0 times, more preferably 1.0 to 4.0 times, and even more preferably 1.5 to 3.0 times as much of the width of the groove portion. Accordingly, it is easier to achieve the effects as described in aspect 5 and aspect 6. Incidentally, in a case in which the first layer includes a plurality of specified groove portions or non-specified groove portions, the portion which overlaps with other specified groove portions, the base portion which is adjacent to other specified groove portions, and the non-specified groove portions, etc., is excluded from the pair of width direction base portions. Further, in a case in which the first layer includes a plurality of specified groove portions, the pair of width direction base portions may be overlapped with other pair of width direction base portions.

In the absorbent article according to the present disclosure, it is preferable that the groove portion further includes the subordinate groove portion which penetrates in the thickness direction of the first layer, in the direction which intersects with the groove portion, and is present so as to be connected to the groove portion through the subordinate groove portion base edge. This is from the viewpoint of the effect which is described in aspect 7.

The subordinate groove portion may or may not include a subordinate groove portion terminal edge on the opposite side of the subordinate groove portion base edge. For example, the subordinate groove portion may be connected to the specified groove portion or the non-specified groove portion which is adjacent to the groove portion that is connected to the subordinate groove portion, or may reach the both end portions in the width direction of the absorbent core. However, it is preferable that the subordinate groove portion includes the subordinate groove portion terminal edge on the opposite side of the subordinate groove portion base edge. This is from the viewpoint of the effect which is described in aspect 8.

In the absorbent article according to the present disclosure, in a case in which the first layer further includes the subordinate groove portion, it is preferable that the second layer further includes the subordinate groove portion corresponding portion which is arranged at the position which overlaps with the subordinate groove portion in the thickness direction, and the average density of the superabsorbent polymers included in the subordinate groove portion corresponding portion is smaller than the average density of the superabsorbent polymers included in each of the pair of width direction base portion corresponding portions. This is from the viewpoint of the effect which is described in aspect 9.

Further, it is preferable that the average density of the superabsorbent polymers included in the subordinate groove portion corresponding portion is smaller than the average density of the superabsorbent polymers included in each of the pair of width direction base portions. This is from the viewpoint of the effect which is described in aspect 10.

The subordinate groove portion corresponding portion includes the superabsorbent polymers with the basis weight of preferably 0 to 0.15 g/cm$^3$, and more preferably 0 to 0.1 g/cm$^3$.

The manufacturing method of the absorbent article according to the present disclosure is not particularly limited, however, for example, the following method may be used.

Incidentally, in the present description, "the conveying direction of a material or a product" is referred to as "the MD direction", "the direction which is orthogonal to the MD direction on a horizontal surface" (that is, the width direction of the manufacturing line) is referred to as "the CD direction", and "the direction which is orthogonal to the MD direction and the CD direction" (that is, the vertical direction of the manufacturing line) is referred to as "the TD direction". Further, the rotation direction of the suction drum 205 is referred to as the RT direction.

Figure 15:
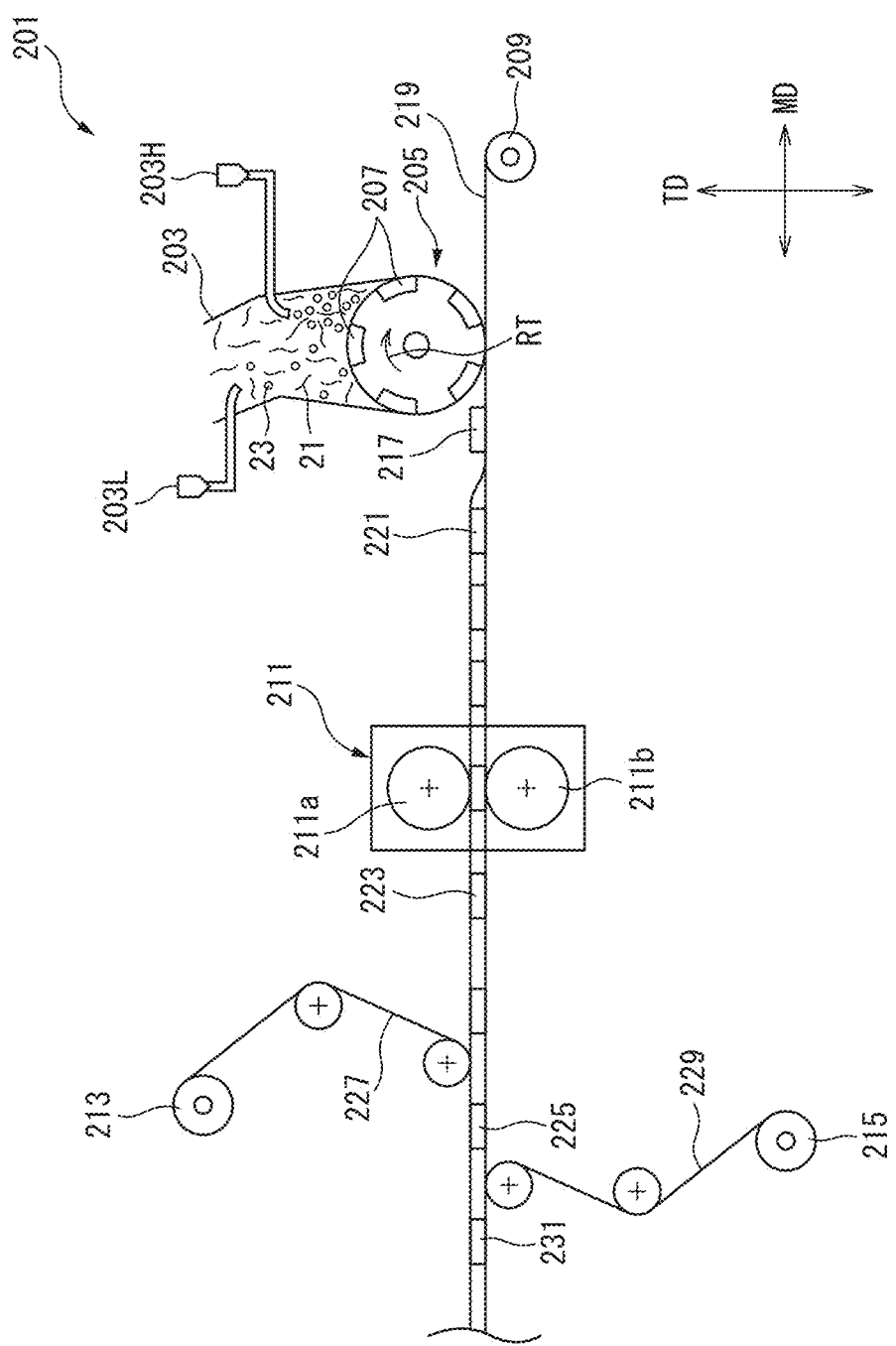
FIG. 15 is a schematic view of the manufacturing device 201 which can manufacture the absorbent core according to the present disclosure.
Figure 16:
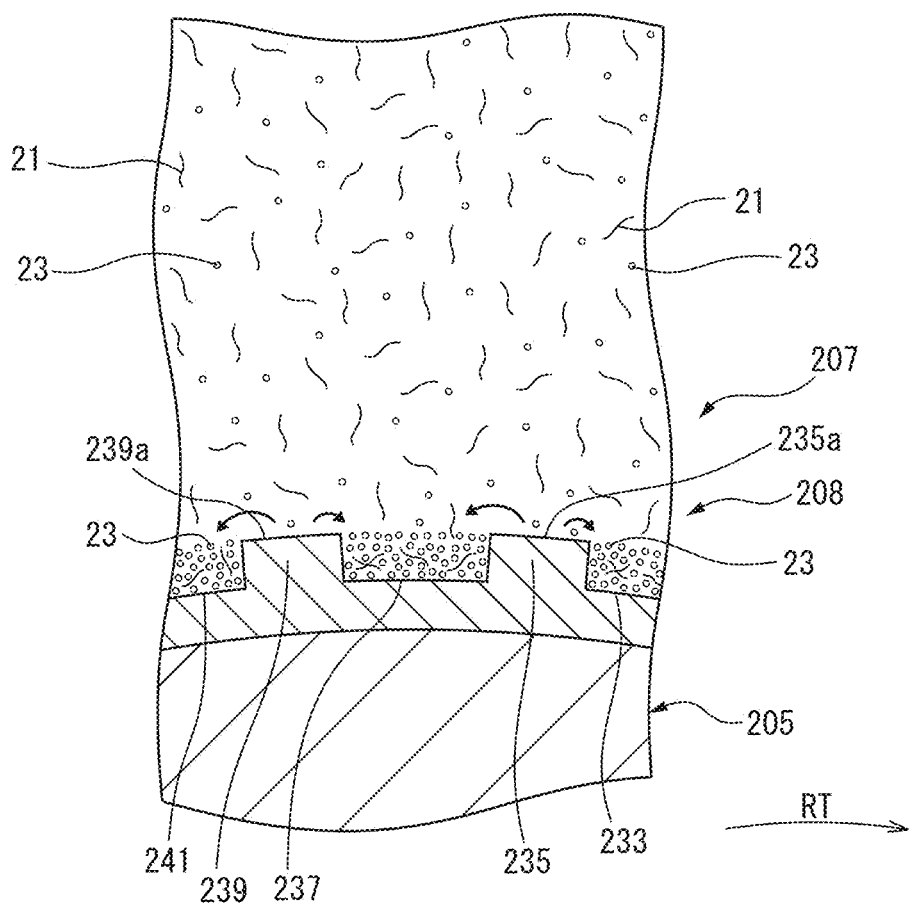
FIG. 16 is an essential portion enlarged end view which schematically shows the state in which the absorbent material is accumulated in the mold member 207 that is provided in the outer peripheral surface of the suction drum 205 of the manufacturing device 201.
Figure 17:
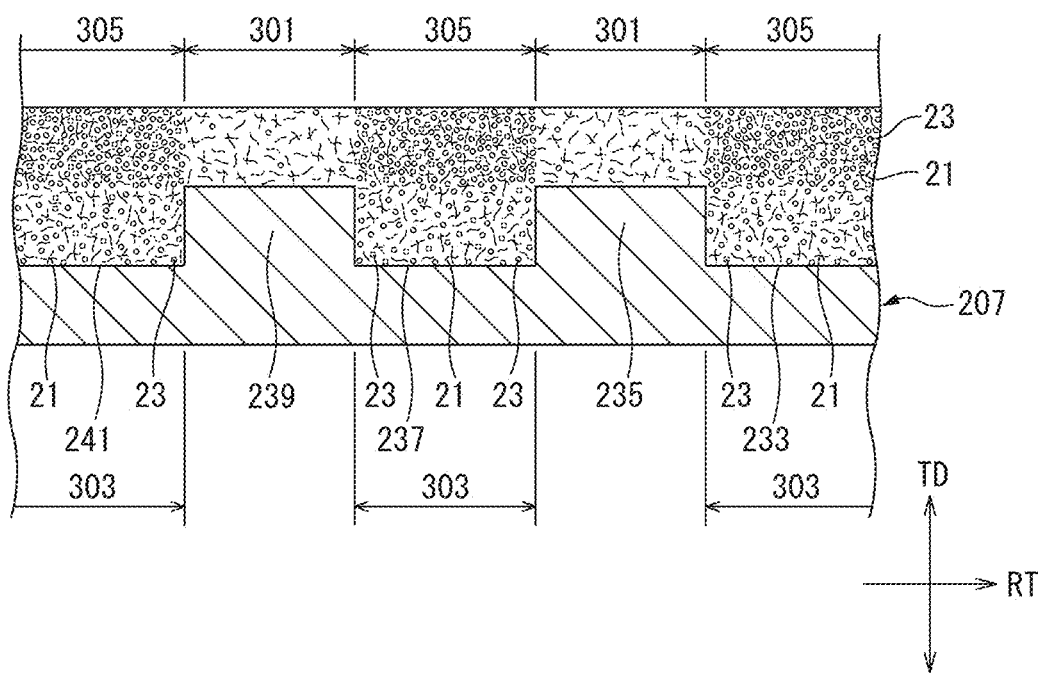
FIG. 17 is an essential portion enlarged end view of the first laminate body 217 which is accumulated in the mold member 207.
Figure 18:
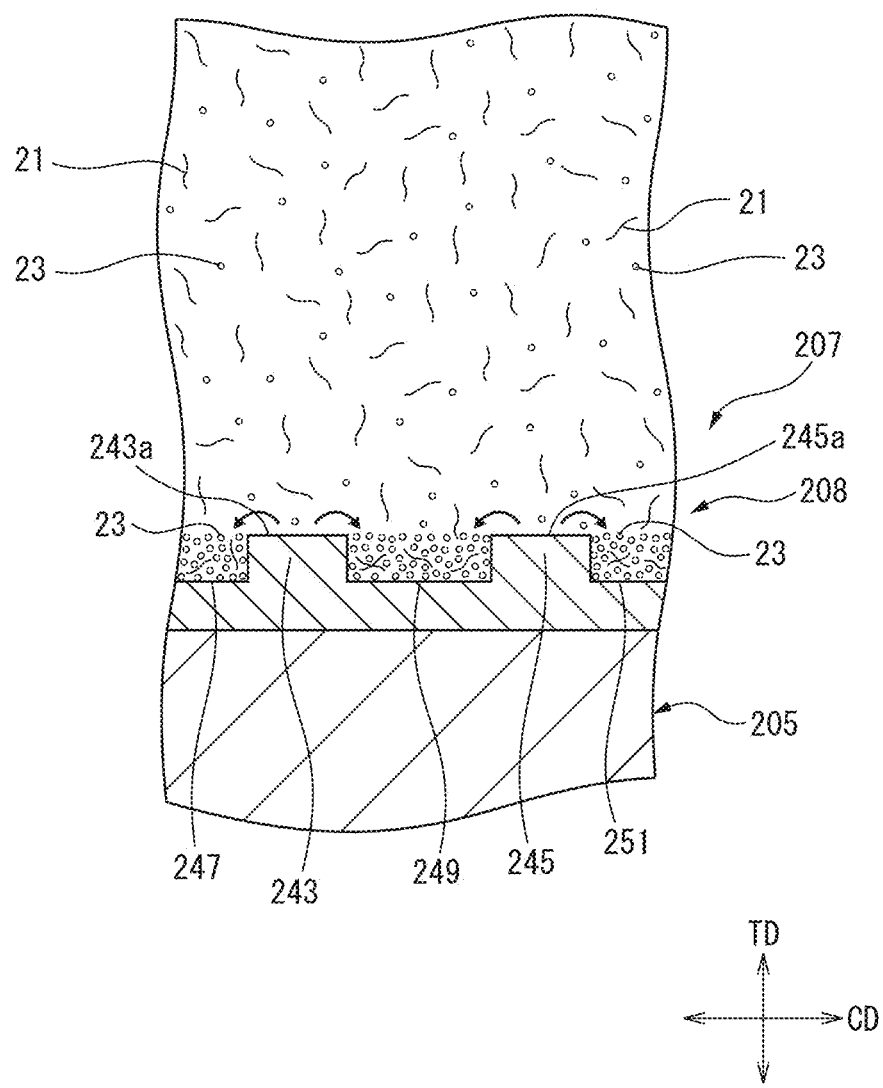
FIG. 18 is an essential portion enlarged end view which schematically shows the state in which the absorbent material is accumulated in the mold member 207 that is provided in the outer peripheral surface of the suction drum 205 of the manufacturing device 201.

FIG. 15 is a schematic view of the manufacturing device which can manufacture the absorbent core according to the present disclosure. FIG. 16 is an essential portion enlarged end view which schematically shows the state in which the absorbent material is accumulated in the mold member 207 that is provided in the outer peripheral surface of the suction drum 205 of the manufacturing device 201. FIG. 17 is an essential portion enlarged end view of the first laminate body 217 which is accumulated in the mold member 207. FIG. 18 is an essential portion enlarged end view which schematically shows the state in which the absorbent material is accumulated in the mold member 207 that is provided in the outer peripheral surface of the suction drum 205 of the manufacturing device 201.

The manufacturing device 201 includes the conveying pipe 203 which conveys the absorbent material that includes the opened pulp fibers 21 and the superabsorbent polymers 23, and the freely rotatable suction drum 205 which sucks the absorbent material that is discharged from the conveying pipe nozzle 203L and the conveying pipe nozzle 203H of the conveying pipe 203 and makes the absorbent material laminate on the plurality of concave mold members 207 which are arranged with a certain interval along the circumferential direction of the outer peripheral surface, whereby forms the first laminate body 217 which is to be the absorbent core 9 of the absorbent body 7 in the later process.

Further, the conveying pipe 203 includes the conveying pipe nozzle 203L which discharges the superabsorbent polymers 23 with a relatively low discharge ratio, and the conveying pipe nozzle 203H which discharges the superabsorbent polymers 23 with a relatively high discharge ratio. In the present embodiment, the mass ratio of the superabsorbent polymers 23 which is included in the conveying pipe nozzle 203L and the conveying pipe nozzle 203H is 30:70.

Further, the manufacturing device 201 includes the unwinding roll 209 for the wrap continuous body 219 which makes the first laminate body 217 be placed on the outer peripheral surface of the suction drum 205 and unwind out the long core wrap continuous body 219 which covers the first laminate body 217 so as to cover the first laminate body 217 by the core wrap continuous body 219, whereby forms the second laminate body 221.

Further, the manufacturing device 201 includes the pressing device 211 which includes the pair of upper and lower press rolls 211a, 211b (in the TD direction) which applies pressure and compresses the second laminate body 221 in the thickness direction.

Still further, the manufacturing device 201 includes the unwinding roll 213 for the liquid permeable sheet continuous body 227 which winds out and makes the long liquid permeable sheet continuous body 227 that configures the liquid permeable sheet 3 be laminated, for one surface of the third laminate body 223 after being subjected to the pressing process (in the case of FIG. 15, the upper surface), in the downstream in the conveying direction MD with respect to the pressing device 211.

Still further, the manufacturing device 201 includes the unwinding roll 215 for the liquid impermeable sheet continuous body 229 which unwinds and makes the long liquid impermeable sheet continuous body 229 that forms the liquid impermeable sheet 5 be joined to the surface on the opposite side of the liquid permeable sheet continuous body 227 in the fourth laminate body 225 formed by the liquid permeable sheet continuous body 227 being laminated on the third laminate body 223 (in the case of FIG. 1t5, the lower surface), whereby forms the fifth laminate body 231.

Incidentally, at the further downstream in the conveying direction MD with respect to the unwinding roll 215 for the liquid impermeable sheet continuous body 229, a cutting device (which is not shown) which cuts the fifth laminate body 231 into the shape of the absorbent article 1 as a product so as to be a single absorbent article 1 (which is not shown), each of the devices that crimps the leakage prevention wall 101, and the tape fastener 109, etc., onto the fifth laminate body 231 (which is not shown) are included, however, since these devices are known in the technical field, the detailed explanation is omitted.

In a case in which the absorbent article 1 is manufactured by using the manufacturing device 201, basically, the first process of forming the first laminate body 217, the second process of forming the second laminate body 221 by covering the first laminate body 217 by the core wrap continuous body 219, and the third process of forming the third laminate body 223 by compressing the second laminate body 221 by the pressing device 211 in thickness direction, are sequentially performed. Further, the fourth process of forming the fourth laminate body 225 by laminating the liquid permeable sheet continuous body 227 on the third laminate body 223, and the fifth process of forming the fifth laminate body 231 by joining the liquid impermeable sheet continuous body 229 to the fourth laminate body 225, are sequentially performed.

In the first process, the absorbent material which includes the pulp fibers 21 and the superabsorbent polymers 23 is supplied to the suction drum 205 through the conveying pipe 203, the absorbent material is laminated on the mold member 207 of the outer peripheral surface of the suction drum 205, whereby the first laminate body 217 is formed. Incidentally, the first laminate body 217 is to eventually configure the absorbent core 9 of the absorbent body 7.

As shown in FIG. 16, the absorbent material is supplied into the mold member 207 from above. The mold member 207 includes in the bottom portion 208 of the mold member 207, the rotation direction depression 233, the rotation direction protrusion 235, the rotation direction depression 237, the rotation direction protrusion 239, and the rotation direction depression 241, from the upstream side of the mold member 207 (the right side of FIG. 16).

<The Formation of the First Layer>

When the absorbent material is supplied to the mold member 207 from the conveying pipe nozzle 203L which discharges the superabsorbent polymers 23 with a relatively low discharge ratio, since the pulp fibers 21 is light and has softness, it is difficult for the pulp fibers 21 to bounce back even when the pulp fibers 21 collide with the rotation direction protrusion 235 and the rotation direction protrusion 239, whereby the pulp fibers 21 are accumulated in the mold member 207 substantially evenly.

On the other hand, at the stage in which the absorbent material begins to be supplied into the mold member 207, the superabsorbent polymers 23 collide with the tip end surface 235a and the tip end surface 239a of the rotation direction protrusion 235 and the rotation direction protrusion 239, respectively, bounce back therefrom, move without staying at the tip end surface 235a and the tip end surface 239a, and reach and are accumulated in the rotation direction depression 233, the rotation direction depression 237, and the rotation direction depression 241.

This is because, in addition to the fact that the superabsorbent polymers 23 are normally granular, the mass of the superabsorbent polymers 23 is relatively large, and due to the suction of the suction drum 205, it is easy to be influenced by the kinetic energy of the superabsorbent polymers 23 themselves, whereby it is easy for the superabsorbent polymers 23 to bounce back when colliding with the tip end surface 235a and the tip end surface 239a of the rotation direction protrusion 235 and the rotation direction protrusion 239, respectively, and it is difficult for the superabsorbent polymers 23 to stay at the position of collision. As described above, the first layer 17 in the absorbent core 9 is to be laminated.

Incidentally, since the suction drum 205 normally rotates in a high speed, since it is relatively easier for the bounced back superabsorbent polymers 23 to move to the downstream side of the mold member 207 (the left side in FIG. 17), it is preferable to form the mold member 207 so that the front body FP of the absorbent core is positioned on the upstream side of the mold member 207 (the right side in FIG. 16). Further, the rotation speed of the suction drum 205 may be set to be slower than the rotation speed when manufacturing an absorbent article normally.

<The Formation of the Second Layer>

Subsequently, the absorbent material is supplied to the mold member 207 from the conveying pipe nozzle 203H which discharges the superabsorbent polymers 23 with a relatively high discharge ratio and is present at a lower position than the conveying pipe nozzle 203L. In the mold member 207, although the pulp fibers 21 are accumulated also in the rotation direction protrusion 235 and the rotation direction protrusion 239, since the superabsorbent polymers 23 are included in a high discharge ratio, when the superabsorbent polymers 23 collide, it is still difficult to absorb the impact thereof even by the softness of the pulp fibers 21, whereby it is easy for the superabsorbent polymers 23 to bounce back. As a result, eventually, as shown in FIG. 17, a plurality of portions in which the average density of the superabsorbent polymers 23 with respect to the absorbent core 9 is different in the RT direction are to be present in the first laminate body 217. As described above, the second layer 19 in the absorbent core 9 is to be laminated.

That is, in the portion which corresponds to the portion directly above the rotation direction protrusion 235 and the rotation direction protrusion 239 in the mold member 207, the average density of the superabsorbent polymers 23 is the smallest since the superabsorbent polymers 23 collide with the tip end surface 235a and the tip end surface 239a of the rotation direction protrusion 235 and the rotation direction protrusion 239, respectively, so as to move, whereby the small density region 301 is formed.

Further, in the portion along the side wall portion of the rotation direction protrusion 235 and the rotation direction protrusion 239 and in the vicinity thereof, since the moved superabsorbent polymers 23 are present, the average density of the superabsorbent polymers 23 is relatively large, whereby the middle density region 303 is formed.

Still further, in the portion which is greatly influenced by the superabsorbent polymers 23 being bounced back by the tip end surface 235a and the tip end surface 239a of the rotation direction protrusion 235 and the rotation direction protrusion 239 in the mold member 207, the average density of the superabsorbent polymers 23 is the largest, whereby the large density region 305 is formed.

Incidentally, the small density region 301 corresponds to the groove portion corresponding portion of the absorbent core according to the present disclosure, the middle density region 303 corresponds to the base portion of the absorbent core according to the present disclosure, and the large density region 305 corresponds to the base portion corresponding portion of the absorbent core according to the present disclosure.

By referring to FIG. 18, the method of forming the width direction base portion and width direction base portion corresponding portion of the absorbent core according to the present disclosure is explained.

The mold member 207 includes in the bottom portion 208 of the mold member 207, the CD direction protrusion 243 and the CD direction protrusion 245, and the CD direction depression 247, the CD direction depression 249, and the CD direction depression 251, which are positioned in the separated manner in the CD direction of the mold member 207.

When the absorbent material is supplied to the mold member 207 from the conveying pipe nozzle 203L which discharges the superabsorbent polymers 23 with a relatively low discharge ratio, since the pulp fibers 21 is light and has softness, it is difficult for the pulp fibers 21 to bounce back even when the pulp fibers 21 collide with the CD direction protrusion 243 and the CD direction protrusion 245, whereby the pulp fibers 21 are accumulated in the mold member 207 substantially evenly.

On the other hand, at the stage in which the absorbent material begins to be supplied into the mold member 207, the superabsorbent polymers 23 collide with the tip end surface 243a and the tip end surface 245a of the CD direction protrusion 243 and the CD direction protrusion 245, respectively, bounce back therefrom, move without staying at the tip end surface 243a and the tip end surface 245a, and reach and are accumulated in the CD direction depression 247, the CD direction depression 249, and the CD direction depression 251. As described above, the first layer 17 in the absorbent core 9 is to be laminated.

Subsequently, the absorbent material is supplied to the mold member 207 from the conveying pipe nozzle 203H which discharges the superabsorbent polymers 23 with a relatively high discharge ratio and is present at a lower position than the conveying pipe nozzle 203L. In the mold member 207, although the pulp fibers 21 are accumulated also in the CD direction protrusion 243 and the CD direction protrusion 245, since the superabsorbent polymers 23 are included in a high discharge ratio, when the superabsorbent polymers 23 collide, it is still difficult to absorb the impact thereof even by the softness of the pulp fibers 21, whereby it is easy for the superabsorbent polymers 23 to bounce back. As a result, a plurality of portions in which the average density of the superabsorbent polymers 23 with respect to the absorbent core (which is not shown) is different in the CD direction are to be present in the first laminate body (which is not shown). As described above, the second layer (which is not shown) in the absorbent core (which is not shown) is to be laminated.

After the first process, the second process is performed in which the first laminate body 217 of the mold member 207 is placed on the core wrap continuous body 219 in a state of an adhesive agent such as a hot-melt adhesive agent, etc., intervening therebetween, by the rotation of the suction drum 205, and the outer peripheral surface of the first laminate body 217 is covered by the core wrap continuous body 219, whereby the second laminate body 221 is formed.

In the second process, the rotating suction drum 205 transfers and places the first laminate body 217 of the mold member 207 on the core wrap continuous body 219 which is wound out from the unwinding roll 209 for the core wrap continuous body 219 and moving in the conveying direction MD. Further, by the bending means which is not shown, the core wrap continuous body 219 is bent in the width direction CD which is orthogonal to the conveying direction MD along the outer peripheral surface of the first laminate body 217, and winds the core wrap continuous body 219 around the first laminate body 217 so that the first laminate body 217 is covered, whereby the long second laminate body 221 is formed.

After the second process is finished, the third process is performed in which the second laminate body 221 is compressed in the thickness direction, whereby the third laminate body 223 is formed.

In the third process, the second laminate body 221 is passed through the pair of press rolls 211a, 211b of the pressing device 211, so that the second laminate body 221 is compressed in the thickness direction TD, whereby the third laminate body 223 is formed.

After the third process is finished, the fourth process is performed in which on the upper surface of the third laminate body 223, the liquid permeable sheet continuous body 227 which is wound out from the unwinding roll 213 for the liquid permeable sheet continuous body 227 is laminated with an adhesive agent such as a hot-melt adhesive agent, etc., intervening therebetween, whereby the long fourth laminate body 225 is formed.

Further, after the fourth process is finished, the fifth process is performed in which to the lower surface of the fourth laminate body 225, the liquid impermeable sheet continuous body 229 which is wound out from the unwinding roll 215 for the liquid impermeable sheet continuous body is joined with an adhesive agent such as a hot-melt adhesive agent, etc., intervening therebetween, whereby the long fifth laminate body 231 is formed.

After the fifth process is finished, the fifth laminate body 231 is cut into the shape of the absorbent article 1 by a cutting device (which is not shown), whereby the absorbent article 1 is formed.

EXAMPLES

Hereinbelow, the present disclosure is explained by mentioning examples, however, the present disclosure is not limited to these examples.

Manufacturing Example 1

The absorbent article 1 according to the first embodiment was manufactured. To be specific, the absorbent core No. 1 with the size of 350 mm×[120 mm (the wide width portion), 80 mm (the narrow width portion)] (the longitudinal direction×the width direction), which includes the pulp fibers (the average basis weight: 250 g/m$^2$) and the superabsorbent polymers (the average basis weight: 250 g/m$^2$) was manufactured. In the absorbent core No. 1, the average basis weight ratio of the superabsorbent polymers in the first layer and the second layer was 30:70. Further, when the absorbent core No. 1 was evaluated by the three-dimensional CT, the average density of the superabsorbent polymers included in the base portion corresponding portion was the largest, the average density of the superabsorbent polymers included in the base portion was the second largest, and the average density of the superabsorbent polymers included in the groove portion corresponding portion was the smallest. The thickness of the absorbent core was 2.0 mm Incidentally, in order to perform the absorption test and the liquid return test under a severe condition and to make it easier to judge the difference of the configuration itself of the absorbent core, superabsorbent polymers with the grade in which the absorption speed is mild were selected.

The absorbent core No. 1 was covered by two pieces of tissue (the basis weight: 16 g/m², 400 mm×150 mm) as the core wrap with the hot-melt adhesive agent sandwiched in between. The absorbent core No. 1 which was covered by two pieces of tissue was pressed by a hydraulic pressing machine, so as to adjust the thickness of the absorbent core, whereby the absorbent body No. 1 was formed.

The liquid permeable sheet (an air-through nonwoven fabric) was adhered on the second layer side of the absorbent body No. 1, and the liquid impermeable sheet (a polyethylene film) was adhered on the first layer side thereof, whereby a simple absorbent article No. 1 was manufactured.

Manufacturing Example 2

In the same manner as the manufacturing example 1, the absorbent core No. 2, the absorbent body No. 2, and the simple absorbent article No. 2 were manufactured, except for the pattern of the groove portion being changed into the deformed pattern of the pattern described in FIG. 12 in which the groove portion 25a and the groove portion 31c are replaced with the groove portion 31a, and the groove portion 25b and the groove portion 31d are replaced with the groove portion 31b (which does not include the terminal edge 27a and the base portion 29a of the groove portion 25a, and the terminal edge 27b and the base portion 29b of the groove portion 25b). [Manufacturing example 3]

In the same manner as the manufacturing example 1, the absorbent core No. 3, the absorbent body No. 3, and the simple absorbent article No. 3 were manufactured, except for the groove portion not being formed.

Example 1, and Comparative Examples and 2

The absorption test and the liquid return test which are defined as follows were performed for the absorbent articles No. 1 to No. 3, and the absorption time and the liquid return amount were evaluated. The results are shown in Table 1.
[The Absorption Test]
(1-1) The absorbent article is set to a U-shaped instrument the side view of which is substantially U-shaped. Incidentally, the absorbent article is set so that the central position of the absorbent body in the longitudinal direction matches the central portion of the U-shaped instrument (the position at which the height is the lowest).
<The First Cycle>
(1-2) 80 mL of artificial urine (the first time) is injected from a burette with the speed of 80 mL/10 sec to the central position of the absorbent body.
(1-3) The time from the start of injection of the artificial urine of the first time until the artificial urine within the U-shaped instrument disappears is recorded as the absorption time (80 mL) (the description in the Table 1 is omitted).
<The Second Cycle>
(1-4) After 10 minutes from the start of injection of the artificial urine of the first time, 80 mL of artificial urine (the second time) is injected from a burette with the speed of 80 mL/10 sec to the central position of the absorbent body.
(1-5) The time from the start of injection of the artificial urine of the second time until the artificial urine within the U-shaped instrument disappears is recorded as the absorption time (160 mL).
<The Third Cycle>
(1-6) The operations of (1-4) and (1-5) are repeated, 80 mL of artificial urine (the third time) is added, and the absorption time (240 mL) is measured.
[The Liquid Return Test]
(2-1) (1-1) to (1-5) of the absorption test is performed, and after 4 minutes from the start of injection of the artificial urine of the second time, the absorbent articles are removed from the U-shaped instrument, the absorbent articles are expanded on an acrylic flat plate so that the liquid permeable sheet is to be the upper surface, and is left still for one minute.
(2-2) After 5 minutes from the start of injection of the artificial urine of the second time, approximately 60 g of filter paper with the size of 100 mm×100 mm is placed still on the liquid permeable sheet of the absorbent articles with the artificial urine injection point as the center. Further, 3.5 kg of weight with the size of 100 mm×100 mm×50 mm (height) is placed still thereon. Incidentally, as for the filter paper, the mass before the test is measured in advance.
(2-3) After 8 minutes from the start of injection of the artificial urine of the second time, the weight is removed, the mass of the filter paper is measured, the mass of the filter paper before the test is subtracted, and the difference is regarded as the liquid return amount (160 mL).
(2-4) (2-1) to (2-3) is performed except for changing "(1-1) to (1-5) of the absorption test is performed" to "(1-1) to (1-6) of the absorption test is performed", and changing "from the start of injection of the artificial urine of the second time" to "from the start of injection of the artificial urine of the third time", whereby the liquid return amount (240 mL) is measured.

Incidentally, the artificial urine is prepared by dissolving 200 g of urea, 80 g of sodium chloride, 8 g of magnesium sulfate, 3 g of calcium chloride, and approximately 1 g of a dye: blue No. 1, in 10 L of ion exchanged water.

TABLE 1

| | Example No. | | |
|---|---|---|---|
| | Example 1 | Comparative example 1 | Comparative example 2 |
| Absorbent article No. | No. 1 | No. 2 | No. 3 |
| Groove portion/ Terminal edge | Present/Present | Present/Absent | Absent |
| Base portion | Present | Absent | Absent |
| Absorption time/second 160 mL | 51 | 69 | 78 |
| 240 mL | 80 | 230 | 285 |
| Liquid return amount/g 160 mL | 1 | 19 | 28 |
| 240 mL | 20 | 45 | 64 |

The invention claimed is:
1. An absorbent article which includes a liquid permeable sheet, an absorbent core that has superabsorbent polymers for absorbing body fluid, and a liquid impermeable sheet, wherein
the absorbent core is sandwiched between the liquid impermeable sheet and the liquid permeable sheet, the absorbent article includes a longitudinal direction that has a front side and a rear side, a width direction, and a thickness direction, and is partitioned into a front body and a rear body, the absorbent core includes a first layer and a second layer which are adjacent to each other in the thickness direction, the first layer includes the superabsorbent polymers, and further includes (i) a groove portion which extends along the longitudinal direction, penetrates in the thickness direction, and includes a terminal edge at a position on the rear side, and (ii) a base portion which is arranged adjacent to the position on the rear side of the groove portion with the terminal edge placed in between, the groove portion and the base portion being arranged at the front body, the second layer includes the superabsorbent polymers, and further includes a groove portion corresponding portion and a base portion corresponding portion at positions which overlap with the groove portion and the base portion in the thickness direction, respectively, the superabsorbent particles of the second layer are distinct from the superabsorbent polymers of the first layer and each of an average density of the superabsorbent polymers included in substantially all of the base portion and an average density of the superabsorbent polymers included in substantially all of the base portion corresponding portion is larger than an average density of the superabsorbent polymers included in the groove portion corresponding portion, and an average density of the superabsorbent polymers included in the first layer is smaller than an average density of the superabsorbent polymers included in the second layer such that a first layer average flow velocity of the body fluid passing through the first layer is greater than a second layer average flow velocity of the body fluid passing through the second layer.

2. The absorbent article according to claim 1, wherein the average density of the superabsorbent polymers included in substantially all of the base portion corresponding portion is larger than the average density of the superabsorbent polymers included in substantially all of the base portion.

3. The absorbent article according to claim 1, wherein the groove portion includes at least one longitudinal groove extending along the longitudinal direction and at least one width groove extending in the width direction which intersects with the longitudinal direction.

4. The absorbent article according to claim 1, wherein the groove portion is arranged toward the rear side so as to approach a longitudinal direction axis line of the absorbent article.

5. The absorbent article according to claim 1, wherein the first layer further includes a pair of width direction base portions which are arranged adjacent to two sides in the width direction of the groove portion, the second layer further includes a pair of width direction base portion corresponding portions which are arranged at positions overlapping with the pair of width direction base portions in the thickness direction, and each of an average density of the superabsorbent polymers included in each of the pair of width direction base portions and the average density of the superabsorbent polymers included in the groove portion corresponding portion is smaller than an average density of the superabsorbent polymers included in each of the pair of width direction base portion corresponding portions.

6. The absorbent article according to claim 5, wherein the average density of the superabsorbent polymers included in the groove portion corresponding portion is smaller than the average density of the superabsorbent polymers included in each of the pair of width direction base portions.

7. The absorbent article according to claim 5, wherein the first layer further includes a subordinate groove portion which penetrates in the thickness direction of the first layer and extends in a direction intersecting with the groove portion, and the subordinate groove portion has a subordinate groove portion base edge connected to the groove portion.

8. The absorbent article according to claim 7, wherein the subordinate groove portion further includes a subordinate groove portion terminal edge on an opposite side of the subordinate groove portion base edge.

9. The absorbent article according to claim 7, wherein the second layer further includes a subordinate groove portion corresponding portion which is arranged at a position overlapping with the subordinate groove portion in the thickness direction, and an average density of the superabsorbent polymers included in the subordinate groove portion corresponding portion is smaller than the average density of the superabsorbent polymers included in each of the pair of width direction base portion corresponding portions.

10. The absorbent article according to claim 9, wherein the average density of the superabsorbent polymers included in the subordinate groove portion corresponding portion is smaller than the average density of the superabsorbent polymers included in each of the pair of width direction base portions.

11. The absorbent article according to claim 1, wherein the first layer is arranged on a clothing side of the absorbent article with respect to the second layer.

12. The absorbent article according to claim 1, wherein the absorbent article further includes a core wrap which is arranged on a surface of the first layer on an opposite side of the second layer, and the core wrap protrudes toward the second layer in the groove portion.

13. The absorbent article according to claim 1, wherein the groove portion includes
at least three longitudinal grooves extending along the longitudinal direction, and
at least two width grooves extending along the width direction and intersecting each of the at least three longitudinal grooves.

14. The absorbent article according to claim 13, wherein the groove portion corresponding portion includes
at least three longitudinal corresponding grooves, and
at least two width corresponding grooves intersecting each of the at least three longitudinal corresponding grooves.

15. The absorbent article according to claim 1, wherein the groove portion and the base portion in the first layer of the absorbent core are sandwiched between the liquid impermeable sheet and the liquid permeable sheet in the thickness direction.

* * * * *